US011801177B2

(12) United States Patent
Nahavandi et al.

(10) Patent No.: US 11,801,177 B2
(45) Date of Patent: Oct. 31, 2023

(54) PATIENT SUPPORT APPARATUSES WITH MOTION CUSTOMIZATION

(71) Applicant: Stryker Corporation, Kalamazoo, MI (US)

(72) Inventors: Kurosh Nahavandi, Portage, MI (US); Placide Nibakuze, Kalamazoo, MI (US); David Buick, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 985 days.

(21) Appl. No.: 16/721,133

(22) Filed: Dec. 19, 2019

(65) Prior Publication Data

US 2020/0197247 A1 Jun. 25, 2020

Related U.S. Application Data

(60) Provisional application No. 62/783,442, filed on Dec. 21, 2018.

(51) Int. Cl.
*A61G 7/018* (2006.01)
*A61G 7/012* (2006.01)
(Continued)

(52) U.S. Cl.
CPC ............ *A61G 7/018* (2013.01); *A61G 7/012* (2013.01); *A61G 7/07* (2013.01); *A61G 13/06* (2013.01);
(Continued)

(58) Field of Classification Search
CPC ........ A61G 7/018; A61G 7/012; A61G 7/002; A61G 7/07; A61G 13/06; A61G 13/02; G16H 40/67
(Continued)

(56) References Cited

U.S. PATENT DOCUMENTS

| 7,487,562 B2 | 2/2009 | Frondorf |
| 8,413,271 B2 | 4/2013 | Blanchard et al. |

(Continued)

FOREIGN PATENT DOCUMENTS

| CA | 3041267 A1 * | 4/2018 | ........... A47C 20/041 |
| EP | 1975750 A2 | 3/2008 | |
| EP | 2345396 B1 | 1/2011 | |

OTHER PUBLICATIONS

Hill-Rom Centrella Smart Bed Manual, Sep. 28, 2017.
(Continued)

*Primary Examiner* — Robert G Santos
(74) *Attorney, Agent, or Firm* — Warner Norcross + Judd LLP

(57) ABSTRACT

A patient support apparatus includes a litter frame, a support deck, an actuator, a user interface, a transceiver, and a controller. The controller is adapted to limit the movement of the actuator to a first range of motion in the absence of receiving a motion limit message from an off-board device via the transceiver or from a local user interface on the patient support apparatus. The controller is further adapted to limit the movement of the actuator to a second and different range of motion after receiving and implementing a motion limit message. The off-board device may be a local server positioned in a healthcare facility, a remote server, or another device. In some embodiments, the patient support apparatus includes a memory with stored data defining the multiple ranges of motion and the controller selects one of the ranges of motion in response to the motion limit message.

8 Claims, 8 Drawing Sheets

(51) Int. Cl.
*A61G 13/06* (2006.01)
*A61G 7/07* (2006.01)
*G16H 40/67* (2018.01)

(52) U.S. Cl.
CPC ......... *G16H 40/67* (2018.01); *A61G 2203/16* (2013.01); *A61G 2203/20* (2013.01); *A61G 2203/36* (2013.01); *A61G 2203/40* (2013.01)

(58) Field of Classification Search
USPC .............................................. 5/611, 600, 11
See application file for complete search history.

(56) References Cited

U.S. PATENT DOCUMENTS

| | | | |
|---|---|---|---|
| 10,410,500 | B2 | 9/2019 | Derenne et al. |
| 10,463,551 | B2 * | 11/2019 | Totemeier ................ A61G 7/07 |
| 10,709,623 | B2 * | 7/2020 | Totemeier .............. A47C 20/08 |
| 2008/0172789 | A1 | 7/2008 | Elliot et al. |
| 2014/0039351 | A1 | 2/2014 | Mix et al. |
| 2015/0000035 | A1 | 1/2015 | Becker et al. |
| 2015/0164722 | A1 | 6/2015 | Roussy et al. |
| 2016/0213537 | A1 | 7/2016 | Hayes et al. |
| 2017/0224559 | A1 * | 8/2017 | Totemeier ................ A61G 7/07 |
| 2018/0110665 | A1 * | 4/2018 | Totemeier ............ A47C 20/041 |
| 2018/0303687 | A1 | 10/2018 | Moreno et al. |
| 2019/0336367 | A1 | 11/2019 | Zerhusen et al. |
| 2020/0197247 | A1 * | 6/2020 | Nahavandi ............. G16H 40/63 |

OTHER PUBLICATIONS

Stryker Operations Manual Epic II Critical Care Bed, Model 2030, Jan. 2010.
Stryker Operations Manual InTouch Critical Care Bed Model FL27, Apr. 2012.

* cited by examiner

PATIENT SUPPORT APPARATUSES WITH MOTION CUSTOMIZATION

CROSS-REFERENCE TO RELATED APPLICATIONS

This application claims priority to U.S. provisional patent application Ser. No. 62/783,442 filed Dec. 21, 2018, by inventors Kurosh Nahavandi et al. and entitled PATIENT SUPPORT APPARATUSES WITH MOTION CUSTOMIZATION, the complete disclosure of which is incorporated herein by reference.

BACKGROUND

The present disclosure relates to patient support apparatuses, such as beds, cots, stretchers, operating tables, recliners, or the like. More specifically, the present disclosure relates to patient support apparatuses that have actuators for moving components of the patient support apparatus.

Existing hospital beds and/or stretchers often include a litter frame whose height is adjustable. Mounted to the litter frame is often a multi-sectioned deck having a head section—also referred to as a Fowler section—that is pivotable between a generally horizontal orientation and a raised orientation. One or more other components of the patient support apparatus may also or alternatively be movable. The movement of the various components of the patient support apparatus is often accomplished through the use of one or more actuators, which may comprise one or more motors, pumps, or other powered devices that drive one or more components of the patient support apparatus.

SUMMARY

According to various embodiments, an improved patient support apparatus is provided that enables a healthcare institution and/or authorized personnel to customize the movement of one or more components of the patient support apparatus. For example, in some embodiments, a patient support apparatus is provided having a litter frame that is movable between a minimum and a maximum height, and the patient support apparatus is further adapted to receive a motion limit message from an authorized off-board device that changes the value of one or both of the minimum or maximum height. In response thereto, the patient support apparatus stops movement of the litter deck at the new minimum or maximum when the user is activating the corresponding height actuator(s). As a result, appropriate personnel at the healthcare facility can customize their patient support apparatuses to have a minimum and/or maximum height. Similarly, patient support apparatuses are provided herein in which a lockout control for pivoting of the Fowler section of the patient support apparatus can be customized to have different angular limits.

According to one embodiment of the present disclosure, a patient support apparatus system is provided that includes a computer device and a patient support apparatus. The computer device is adapted to transmit a motion limit message in response to an input from an authorized administrator. The patient support apparatus is positioned physically apart from the computer device and includes a litter frame, a support deck, an actuator, a transceiver, and a controller. The support deck is supported on the litter frame and configured to support a patient thereon. The actuator is adapted to move a component of the patient support apparatus. The user interface includes a movement control adapted to cause the actuator to move the component when the movement control is activated. The transceiver is adapted to communicate with the computer device and to receive the motion limit message from the computer device. The controller communicates with the transceiver, the actuator, and the user interface. The controller is further adapted to prevent movement of the actuator outside of a first range of motion prior to receiving the motion limit message, and to prevent movement of the actuator outside of a second range of motion after receiving the motion limit message. The first range of motion is different from the second range of motion.

According to other aspects of the present disclosure, the component of the patient support apparatus is a pivotable backrest section of the support deck, the first range of motion defines a first minimum angle, and the second range of motion defines a second minimum angle different from the first minimum angle. In such embodiments, the patient support apparatus further comprises a lockout control in communication with the controller. The controller prevents movement of the actuator outside of the first or second ranges only when the lockout control has been activated by a user, and allows movement outside of the first or second ranges of motion when the lockout control has not been activated.

In some embodiments, the component moved by the actuator is the litter frame and the first range of motion limits lowering of a height of the litter frame below a first limit and the second range of motion limits lowering of the height of the litter frame below a second limit.

A memory is included in some embodiments of the patient support apparatus in which first and second setting data is stored. The first setting data defines the first range of motion and the second setting data defines the second range of motion. The memory may also include third setting data that defines a third range of motion wherein the controller is further adapted to prevent movement of the actuator outside of the third range of motion after receiving a second motion limit message. The third range of motion is different from both the first and the second ranges of motion.

In some embodiments, an identifier such as an icon, graphic, text, etc. is positioned adjacent to the movement control. The identifier provides an indication of a function of the movement control and the identifier remains the same both before and after receiving the motion limit message. In other embodiments, the identifier is changed by the controller after receiving the motion limit message.

In some embodiments, the patient support apparatus includes a display adapted to display a first graphical representation of the component moved by the actuator and a second graphic representation of the component. The controller is further adapted to display the first graphical representation of the component before receiving the motion limit message and to display the second graphical representation of the component after receiving the motion limit message. The first graphical representation of the component is different from the second graphical representation of the component. In some embodiments, the first graphical representation depicts the component at a limit of the first range of motion (e.g. a litter frame at its lowest height before receiving the motion limit message) and the second graphical representation depicts the component at a limit of the second range of motion (e.g. a litter frame at its lowest height after receiving the motion limit message).

According to another embodiment of the present disclosure, a patient support apparatus is provided that includes a base, a litter frame, an actuator, a movement control, a memory, and a controller. The litter frame is supported on the base. The support deck is supported on the litter frame and configured to support a patient thereon. The actuator is adapted to raise and lower the litter frame surface with respect to the base. The movement control is adapted to cause the actuator to move the litter frame when the movement control is activated by a user. The memory includes a first setting and a second setting stored therein. The first setting corresponds to a first range of motion for the litter frame and the second setting corresponds to a second range of motion for the litter frame. The controller communicates with the memory, the actuator, and the movement control. The controller is adapted to select the first setting or the second setting and to prevent movement of the litter frame outside the first range of motion if the controller selects the first setting and to prevent movement of the litter frame outside the second range of motion if the controller selects the second setting.

According to other aspects, the patient support apparatus further comprises a transceiver adapted to communicate with an external device and to receive a motion limit message from the external device. The controller selects the first setting or the second setting based on the motion limit message. In some embodiments, the external device is a server on, or in communication with, a healthcare facility computer network.

The motion limit message, in some embodiments, includes at least one of the first setting and the second setting and the controller is adapted to store the at least one of the first setting and the second setting in the memory.

The first range of motion defines a first minimum height and the second range of motion defines a second minimum height, in some embodiments. In such embodiments, the controller is adapted to prevent lowering of the litter frame below the first minimum height when the controller selects the first setting and to prevent lowering of the litter frame below the second minimum height when the controller selects the second setting.

In some embodiments, the patient support apparatus further includes a transceiver adapted to communicate with an external device. The controller is configured to select the first setting in the absence of receiving a motion limit message from the external device instructing the controller to select the second setting.

The patient support apparatus may further comprise a display adapted to display a graphical representation of the litter frame. In such embodiments, the controller may further be adapted to display the graphical representation in a first manner when the controller selects the first setting and to display the graphical representation in a second manner when the controller selects the second setting. The first manner may include displaying the graphical representation of the litter frame at a first minimum height and the second manner may include displaying the graphical representation of the litter frame at a second minimum height.

In some embodiments, the patient support apparatus may further comprise a backrest actuator adapted to pivot a backrest of the support deck, a lockout control, and a memory. The lockout control is adapted to be activated by the user. The memory includes a third setting corresponding to a third range of motion for the backrest and a fourth setting corresponding to a fourth range of motion for the backrest. The controller is further adapted to select the third or the fourth setting when the lockout control is activated. The controller prevents pivoting of the backrest outside the third range of motion if the controller selects the third setting and the controller prevents pivoting of the backrest outside the fourth range of motion if the controller selects the fourth setting. The controller may further be configured to prevent pivoting of the backrest outside a fifth range of motion if the lockout control is not activated. The fifth range of motion is larger than both the third and fourth ranges of motion.

According to another embodiment of the present disclosure, a patient support apparatus is provided that includes a base, a litter frame, a support deck, an actuator, a movement control, a memory, a lockout control, and a controller. The litter frame is supported on the base and the support deck is supported on the litter frame. The support deck is configured to support a patient thereon and includes a pivotable backrest. The actuator is adapted to pivot the backrest over a full range of motion. The movement control is adapted to cause the actuator to pivot the backrest when the movement control is activated by a user. The memory includes a first setting and a second setting stored therein. The first setting corresponds to a first restricted range of motion of the backrest and the second setting corresponds to a second restricted range of motion of the backrest. Both the first and second restricted ranges of motion are less than the full range of motion. The lockout control is adapted to prevent pivoting of the actuator outside the first or second restricted ranges of motion when activated. The controller communicates with the memory, the movement control, the lockout control, and the actuator. The controller is adapted to allow pivoting of the backrest over the full range of motion if the lockout control is not activated, to select the first or second setting if the lockout control is activated, and to prevent pivoting of the backrest outside the first restricted range of motion if the controller selects the first setting and to prevent pivoting of the backrest outside the second restricted range of motion if the controller selects the second setting.

According to other aspects, the patient support apparatus may further comprise a transceiver adapted to communicate with an external device and to receive a motion limit message from the external device. The controller selects the first setting or the second setting based on the motion limit message. In some embodiments, the motion limit message includes at least one of the first setting and the second setting and the controller is adapted to store the at least one of the first setting and the second setting in the memory.

In some embodiments, the first range of motion limits reclining of the backrest beyond a first angle and the second range of motion limits reclining of the backrest beyond a second angle.

In some embodiments, the patient support apparatus further comprises a display adapted to display a graphical representation of the backrest, and the controller is further adapted to display the graphical representation in a first manner when the controller selects the first setting and to display the graphical representation in a second manner when the controller selects the second setting. The first manner may include displaying the graphical representation of the backrest at a first angular orientation and the second manner may include displaying the graphical representation of the backrest at a second angular orientation.

According to some embodiments, the patient support apparatus further comprises a lift actuator adapted to raise and lower the litter frame. In such embodiments, the memory further includes a third setting corresponding to a third range of motion for the litter frame and a fourth setting corresponding to a fourth range of motion for the litter frame. The controller prevents moving the litter frame outside the third range of motion if the controller selects the third setting and the controller prevents moving the litter frame outside the fourth range of motion if the controller selects the fourth setting.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
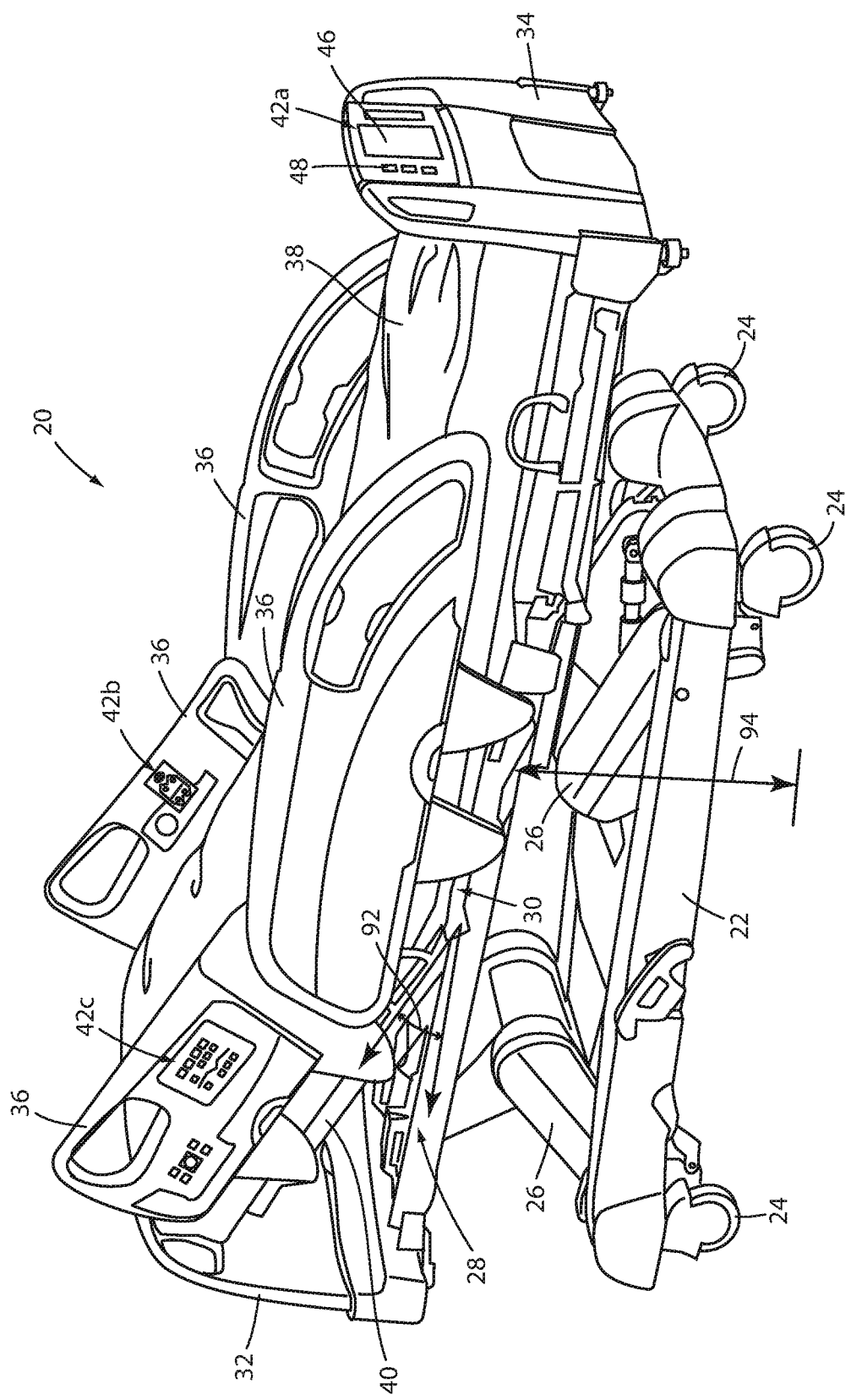
FIG. 1 is a perspective view of a patient support apparatus according to one embodiment of the disclosure.

An illustrative patient support apparatus 20 that may incorporate one or more aspects of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a gurney, a recliner, or any other structure capable of supporting a patient that may be used during times when the patient is not accompanied by a caregiver. For purposes of the following written description, patient support apparatus 20 will be described as a bed with the understanding the following written description applies to these other types of patient support apparatuses.

In general, patient support apparatus 20 includes a base 22 having a plurality of wheels 24, a lift subsystem comprising a pair of lifts 26 supported on the base, a litter frame 28 supported on the lifts 26, and a support deck 30 supported on the litter frame 28. Patient support apparatus 20 further includes a headboard 32, a footboard 34, and a plurality of siderails 36. Siderails 36 are all shown in a raised position in FIG. 1 but are each individually movable to a lower position in which ingress into, and egress out of, patient support apparatus 20 is not obstructed by the lowered siderails 36. In some embodiments, siderails 36 may be moved to one or more intermediate positions as well.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end and a foot end, each of whose height can be independently adjusted by the nearest lift 26. Patient support apparatus 20 is designed so that when an occupant lies thereon, his or her head will be positioned adjacent the head end and his or her feet will be positioned adjacent the foot end.

Litter frame 28 provides a structure for supporting support deck 30, the headboard 32, footboard 34, and siderails 36. Support deck 30 provides a support surface for a mattress 38, or other soft cushion, so that a person may lie and/or sit thereon. Support deck 30 is made of a plurality of sections, some of which are pivotable about generally horizontal pivot axes. In the embodiment shown in FIG. 1, support deck 30 includes a head section 40, which is also sometimes referred to as a Fowler section or a backrest section. Head section 40 is pivotable about a generally horizontal pivot axis between a generally horizontal orientation (not shown in FIG. 1) and a plurality of raised positions (one of which is shown in FIG. 1). Support deck 30 may include additional sections that are pivotable about one or more horizontal pivot axes, such as an upper leg or thigh section and/or a lower leg or foot section (not labeled).

Patient support apparatus 20 further includes a plurality of user interfaces 42 that enable a user of patient support apparatus 20, such as a patient and/or an associated caregiver, to control one or more aspects of patient support apparatus 20. In the embodiment shown in FIG. 1, patient support apparatus 20 includes a footboard user interface 42*a*, a pair of inner siderail user interfaces 42*b* (only one of which is visible), and a pair of outer siderail user interfaces 42c (only one of which is visible). Footboard user interface 42a and outer siderail user interfaces 42c are intended to be used by caregivers, or other authorized personnel, while inner siderail user interfaces 42b are intended to be used by the patient associated with patient support apparatus 20. Not all of the user interfaces 42 include the same controls and/or functionality. In the illustrated embodiment, footboard user interface 42a includes a substantially complete set of controls for controlling patient support apparatus 20 while user interfaces 42b and 42c include a selected subset of those controls. As will be discussed in greater detail below, in one embodiment, footboard user interface 42a and/or outer siderail user interface 42c include a Fowler angle lockout control that is not included on inner siderail user interface 42b. As will also be discussed in greater detail below, one or more of any of user interfaces 42a, b, and/or c may include a height adjustment control that, when activated, changes a height of litter frame 28 relative to base 22.

In addition to these controls, user interfaces 42a and/or 42c may include controls for allowing a user to do one or more of the following: activate and deactivate a brake for wheels 24, arm the exit detection system, take a weight reading of the patient, activate and deactivate a propulsion system, and communicate with a healthcare facility computer network installed in the healthcare facility in which patient support apparatus 20 is positioned. Inner siderail user interfaces 42b may also include a nurse call control that enables a patient to call a nurse. A speaker and microphone are included on, or adjacent to, inner siderail user interface 42b in order to allow the patient to aurally communicate with the remotely positioned nurse.

Footboard user interface 42a is implemented in the embodiment shown in FIG. 1 as a touchscreen display 46 having a plurality of dedicated controls 48 positioned alongside the touchscreen display 46. Dedicated controls 48 may be implemented as buttons, dials, switches, or other devices. Either or both of user interfaces 42b or 42c may also include a display for displaying information regarding patient support apparatus 20, and such a display may be a touchscreen in some embodiments. Alternatively, any one or more of user interfaces 42a-c may omit a touchscreen display and instead include only dedicated controls 48, or some other form of non-display controls.

The mechanical construction of those aspects of patient support apparatus 20 not explicitly described herein may be the same as, or nearly the same as, the mechanical construction of the Model FL27 InTouch Critical Care bed manufactured and sold by Stryker Corporation of Kalamazoo, Michigan. This mechanical construction is described in greater detail in the Stryker Maintenance Manual for the Model FL27 InTouch Critical Care Bed (Version 2.4; 2131-409-002 REV B), published by Stryker Corporation of Kalamazoo, Michigan, the complete disclosure of which is incorporated herein by reference. It will be understood by those skilled in the art that those aspects of patient support apparatus 20 not explicitly described herein can alternatively be designed with other types of mechanical constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of those aspects of patient support apparatus 20 not explicitly described herein may also take on forms different from what is disclosed in the aforementioned references.

Figure 2:
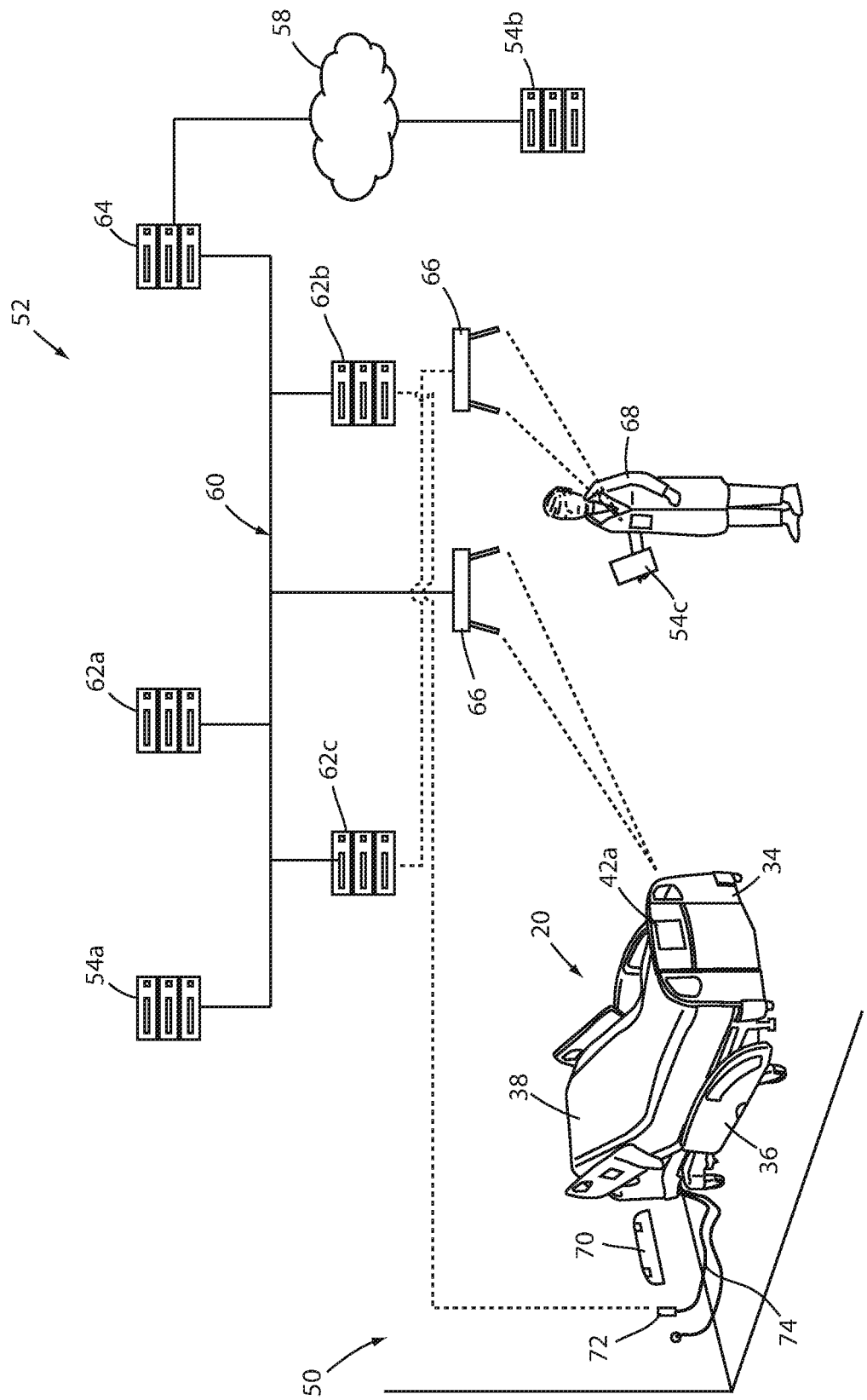
FIG. 2 is a perspective view of a patient support apparatus system according to one embodiment showing the patient support apparatus of FIG. 1 in communication with a local area network of a healthcare facility and other devices.

FIG. 2 illustrates a patient support apparatus system 52 according to one aspect of the present disclosure. Patient support apparatus system 52 includes one or more patient support apparatuses 20 and an external device 54 that is remotely positioned from, and in communication with, patient support apparatus 20. As will be discussed more below, in some embodiments the remotely positioned device is a patient support apparatus server 54a positioned within the healthcare facility, while in other embodiments the remote device is a patient support apparatus server 54b that is positioned remotely from the healthcare facility but still in communication with the patient support apparatus 20 via the Internet 58, while in still other embodiments, the remote device is a mobile electronic device 54c, such as, but not limited to a smart phone, a tablet, a laptop, or the like.

Patient support apparatus 20 is shown in FIG. 2 positioned in a room 50 of a representative example of a healthcare facility. FIG. 2 also depicts patient support apparatus 20 in communication with a representative example of a local area network 60 of the healthcare facility. It will be understood that the precise structure and contents of the local area network 60 will vary from healthcare facility to healthcare facility. As shown, local area network includes a plurality of servers 62, including a conventional Admission, Discharge, and Tracking (ADT) server 62a, a conventional nurse call system server 62b, and a conventional Electronic Medical Records server 62c. Local area network 60 also includes a conventional Internet Gateway 64 that couples local area network 60 to the Internet 56, thereby enabling the servers 54a and/or 62, patient support apparatuses 20, and other applications on network 60 to communicate with computers outside of the healthcare facility, such as, but not limited to, the geographically remote server 54b (which, in at least some embodiments, is operated under the control of the manufacturer of patient support apparatuses 20). Still further, local area network 60 includes a plurality of conventional wireless access points 66 and the local patient support apparatus server 54a.

ADT server 62a stores patient information, including the identity of patients and the corresponding rooms 50, 50a, 50b . . . and/or bays within rooms to which the patients are assigned. Nurse call server 62b communicates with caregivers and, in some embodiments, forwards alerts and/or other communications to portable wireless devices carried by caregivers and/or to audio stations positioned within patient rooms 50. EMR server 62c stores the patients' electronic medical records. Patient support apparatus server 54a receives information from patient support apparatuses 20 and sends messages and/or data back to patient support apparatuses 20. As will be discussed in greater detail below, at least one of the messages that patient support apparatus server 54a is adapted to send to one or more patient support apparatuses 20 is a motion limit message. Patient support apparatus server 54a may further be configured to share data received from the patient support apparatuses 20 with other servers 62 on the network 60 and/or with other servers located geographically remote from the healthcare facility (via Internet 58).

Wireless access points 66 are configured, in at least some embodiments, to operate in accordance with any one or more of the IEEE 802.11 standards (e.g. 802.11g, 802.11n, 802.11ah, etc.). As such, any mobile electronic devices, such as device 54c, that is configured with Wi-Fi capabilities, and that has the proper authorization credentials (e.g. password, SSID, etc.), can access local area network 60. As will be discussed in greater detail below, each patient support apparatus 20 is equipped, in at least some embodiments, with a Wi-Fi transceiver than enables them to communicate with local area network 60 and, more particularly, to send messages to, and receive messages from, patient support apparatus server 54a (and/or remote patient support apparatus server 54b and/or one or more mobile electronic devices 54c). Alternatively, or additionally, patient support apparatuses 20 may include a wired port for coupling a wired cable (e.g. a Category 5, Category 5e, Category 6, etc.) between the patient support apparatus 20 and one or more routers/gateways/switches, etc. of network 60, thereby allowing patient support apparatuses 20 to communicate via wired communications with remote devices 54a, b, c, etc.

In still other embodiments, one or more of the patient support apparatuses 20 are equipped with alternative wireless transceivers enabling them to communicate directly with patient support apparatus server 54a via an antenna and transceiver that is directly coupled to server 54a and separate from LAN 60, thereby allowing patient support apparatuses 20 to bypass LAN in their communications with server 54a. One example of patient support apparatuses equipped to communicate directly with a server on a healthcare facility's local area network without utilizing the LAN is disclosed in commonly assigned U.S. patent application Ser. No. 15/831,466 filed Dec. 5, 2017, by inventors Michael Hayes and entitled NETWORK COMMUNICATION FOR PATIENT SUPPORT APPARATUSES, the complete disclosure of which is incorporated herein by reference. In some embodiments, patient support apparatuses 20 include communication modules, such as the communication modules 66 disclosed in the aforementioned '466 application, and patient support apparatus server 54a is coupled directly to a receiver, such as enterprise receiver 90 disclosed in the aforementioned '466 application. In such embodiments, patient support apparatuses 20 are able to both send and receive messages directly to and from server 54a without utilizing access points 66 or any of the hardware of network 60 (other than server 54a). In still other embodiments, patient support apparatuses 20 may communicate with any of remote devices 54a, 54b, and/or 54c using any of the other communication methods and devices disclosed in the '466 patent application.

The illustrated network 60 is shown to be in communication with remote server 54b and a portable electronic device 54c carried by a caregiver 68. Remote server 54b and portable electronic device 54c may perform any one or more of the functions carried out by local server 54a. More specifically, any one or more of the remote devices 54a, 54b, and/or 54c are adapted to execute a motion limit software application that, in response to a user inputting a selected motion limit, sends out motion limit messages to one or more of the patient support apparatuses 20 positioned within the healthcare facility. In response thereto, the patient support apparatuses 20 adjust the range of motion of at least one of their actuators. The sending of motion limit messages and their processing by patient support apparatuses 20 is discussed in greater detail below.

Network 60 may include additional structures not shown, such as, but not limited to, one or more conventional work flow servers and/or charting servers that assign, monitor, and/or schedule patient-related tasks to particular caregivers, and/or one or more conventional communication servers that forward communications to particular individuals within the healthcare facility, such as via one or more portable devices (smart phones, pagers, beepers, laptops, etc.). The forwarded communications may include data and/or alerts that originate from patient support apparatuses 20.

As shown in FIG. 2, patient support apparatus system 52 includes one or more locators 70 that are mounted at fixed and known locations throughout the healthcare facility. Locators 70 broadcast a wireless, short range signal that contains a unique identifier. The short range signal, in some embodiments, is broadcast via an infrared transmitter and is only detectable by receivers positioned within several feet of the locator 70. Patient support apparatuses 20 include a receiver adapted to detect the signals transmitted from locators 70. Patient support apparatuses 20 forward the received signal, including the unique ID of the locator 70, to patient support apparatus server 54a. Patient support apparatus server 54a includes a table, or has access to a table, that correlates locator IDs to locations within the healthcare facility. Patient support apparatus server 54a is thereby able to determine the location of each patient support apparatus 20 within the healthcare facility (at least all of those that are positioned adjacent a locator 70).

In some embodiments, locators 70 function both as locators and as wireless links to a nurse call outlet 72 integrated into the adjacent headwall. When equipped with this dual function, patient support apparatuses 20 may omit a nurse call cable 74 that runs between the patient support apparatus 20 and the nurse call outlet 72, yet still be able to communicate with the nurse call system server 62b. In the illustrated embodiment of FIG. 2, however, patient support apparatus 20 includes a nurse call cable 74 that communicatively couples the patient support apparatus 20 to nurse call outlet 72, thereby enabling the patient support apparatus 20 to communicate directly with the nurse call system. Further details about the function of locators 70, whether operating solely as locators or both as locators and wireless portals to the nurse call system outlets 72, may be found in any of the following commonly assigned U.S. patent references: U.S. Pat. No. 8,102,254 issued Jan. 24, 2012 to Becker et al. and entitled LOCATION DETECTION SYSTEM FOR A PATIENT HANDLING DEVICE; patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION; patent application Ser. No. 62/600,000 filed Dec. 18, 2017, by inventor Alex Bodurka, and entitled SMART HOSPITAL HEADWALL SYSTEM; and patent application Ser. No. 62/598,787 filed Dec. 14, 2017, by inventors Alex Bodurka et al. and entitled HOSPITAL HEADWALL COMMUNICATION SYSTEM, the complete disclosures of all of which are incorporated herein by reference.

Figure 3:
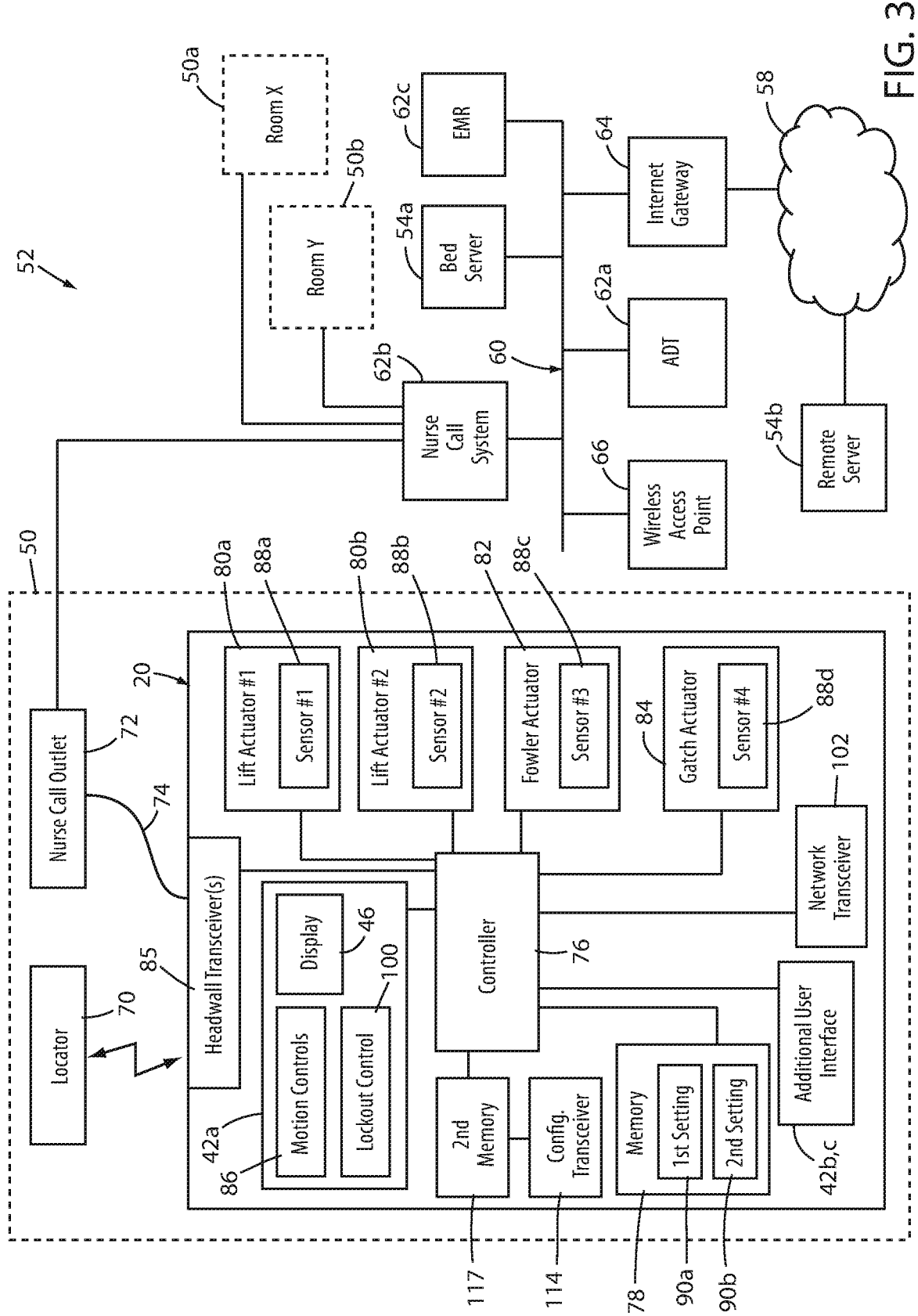
FIG. 3 is a schematic diagram of the patient support apparatus system of FIG. 2.

FIG. 3 illustrates in greater detail the main components of patient support apparatus 20, as well as several structures commonly found in rooms of healthcare facilities. As shown therein, patient support apparatus 20 includes a controller 76, a memory 78, a first lift actuator 80a, a second lift actuator 80b, a Fowler actuator 82, a gatch actuator 84, one or more headwall transceivers 85, a network transceiver 102, a second memory 117, a configuration transceiver 114, user interface 42a, and one or more additional user interfaces 42b, 42c, etc. It will be understood by those skilled in the art that patient support apparatus 20 is depicted in FIG. 3 as including a complete set of components for practicing all of the functions described herein, but that it is not necessary according to the present disclosure for each patient support apparatus 20 to be able to practice all such functions. Thus, one or more of the components of patient support apparatus 20 may be omitted without departing from the principles of the present disclosure. By way of a non-exhaustive list of several examples, patient support apparatus 20 may be modified to omit any one or more of the following devices: second memory 117, configuration transceiver 114, gatch actuator 84, and headwall transceiver(s) 85. Still other omissions can be made.

Patient support apparatus 20 may also include a plurality of additional features and/or components that are not illustrated in FIG. 3. Such additional features may include, but are not limited to, a scale/exit detection system that is adapted to determine a weight of a patient positioned on support deck 30 and/or when the patient is moving and is likely to exit patient support apparatus 20. The particular structural details of the exit detection system can vary widely. In some embodiments, the scale/exit detection system includes a plurality of load cells arranged to detect the weight exerted on litter frame 28. Using the known position of each of the load cells, the controller 76 determines a center of gravity of the patient and monitors the center of gravity for movement beyond one or more thresholds. One method of computing the patient's center of gravity from the output of such load cells is described in more detail in commonly assigned U.S. Pat. No. 5,276,432 issued to Travis and entitled PATIENT EXIT DETECTION MECHANISM FOR HOSPITAL BED, the complete disclosure of which is incorporated herein by reference. Other systems for determining a patient's weight and/or detecting a patient's exit from patient support apparatus 20 may alternatively be used.

Controller 76 (FIG. 3) is constructed of any electrical component, or group of electrical components, that are capable of carrying out the functions described herein. In many embodiments, controller 76 is one or more conventional microcontrollers, although not all such embodiments need include a microcontroller. In general, controller 76 includes any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controller 76 in carrying out the functions described herein, as well as the data necessary for carrying out these functions, are stored in memory 78, and/or in another memory accessible to controller 76.

Controller 76 communicates with headwall transceiver 85 in order to determine its current location from a nearby locator 70, as discussed above. Headwall transceiver 85 also includes a transceiver for sending and receiving signals to and from nurse call outlet 72. In some embodiments, the headwall transceiver 85 is adapted to communicate wirelessly with the nurse call outlet, while in other embodiments the headwall transceiver 85 is adapted to communicate via a nurse call cable 74 with nurse call outlet 72. When communicating wirelessly, headwall transceiver 85 may utilize any of the communication techniques and structures disclosed in the following patent applications, which were previously incorporated herein by reference: patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION; patent application Ser. No. 62/600,000 filed Dec. 18, 2017, by inventor Alex Bodurka, and entitled SMART HOSPITAL HEADWALL SYSTEM; and patent application Ser. No. 62/598,787 filed Dec. 14, 2017, by inventors Alex Bodurka et al. and entitled HOSPITAL HEADWALL COMMUNICATION SYSTEM. When communicating by wire, headwall transceiver 85 may include a cable interface having a plurality of switches of the type disclosed in more detail in commonly assigned U.S. patent application Ser. No. 15/945,437 filed Apr. 4, 2018, by inventors Krishna Bhimavarapu et al. and entitled PATIENT SUPPORT APPARATUSES WITH RECONFIGURABLE COMMUNICATION, the complete disclosure of which is incorporated herein by reference.

Controller 76 further communicates with network transceiver 102 (FIG. 3) which, in at least one embodiment, is a Wi-Fi radio and communication module adapted to wirelessly communicate with wireless access points 66. In other embodiments, network transceiver 102 may include, either additionally or in lieu of the Wi-Fi radio and communication module, an Ethernet port or other port for coupling a network cable to patient support apparatus 20. Regardless of the specific structure included with network transceiver 102, controller 76 is able to communicate with remote devices 54a, 54b, and/or 54c via network transceiver 102. That is, network transceiver 102 allows controller 76 to communicate with local area network 60, and each of devices 54a, 54b, and/or 54c are likewise configured to communicate with local area network 60, thereby enabling devices 54 and patient support apparatuses 20 to communicate with each other.

First and second lift actuators 80a and 80b (FIG. 3) are components of lifts 26 and are configured to raise and lower litter frame 28 with respect to base 22. A first one of lift actuators 80a powers a first one of the lifts 26 positioned adjacent a head end of patient support apparatus 20 and a second one of lift actuators 80b powers a second one of the lifts 26 positioned adjacent a foot end of patient support apparatus 20. Lift actuators 80a and 80b, along with Fowler actuator 82 and gatch actuator 84, may be conventional linear actuators having electric motors therein that, when driven, expand or contract the length of the linear actuator, thereby moving the associated components of patient support apparatus 20 (e.g. lifts 26, Fowler section 40, and gatch section (unlabeled)).

Fowler actuator 82 is adapted to pivot head section 40 (also known as a Fowler section) about a generally horizontal pivot axis such that a person's back and head can be pivoted to different orientations when lying on patient support deck 30. Gatch actuator 84 is adapted to pivot a joint between an upper leg section (e.g. thigh section) and a lower leg section (or foot section) of support deck 30, thereby allowing a patient's knees to be selectively lifted from a horizontal orientation while positioned on support deck 30. All of the actuators 80a, 80b, 82, and 84 are operated by one or more motion controls 86 that are included in one or more of the user interfaces 42. In some embodiments, each user interface 42 includes a motion control 86 for operating each of the actuators 82 and 84, or each set of actuators 80a and 80b (actuators 80a and 80b are operated simultaneously and typically do not have an associated motion control 86 for each individual actuator 80a and 80b). In other embodiments, only a subset of the user interfaces 42 includes a motion control 86 for the actuators and sets of actuators. For example, in some embodiments, only the user interfaces 42 associated with a caregiver (e.g. user interfaces 42a and 42c) include a motion control 86 for changing the height or orientation of litter frame 28 (e.g. controlling lift actuators

80*a* and 80*b*), while the user interface 42*b* associated with a patient does not include such a motion control 86.

Regardless of which specific set of motion controls 86 a specific user interface 42 includes, each actuator 80*a*-*b*, 82, and 84 includes at least one associated sensor 88. More specifically, first lift actuator 80*a* includes a first sensor 88*a*; second lift actuator 80*b* includes a second sensor 88*b*; Fowler actuator 82 includes a third sensor 88*c*; and gatch actuator 84 includes a fourth sensor 88*d*. Each of the sensors 88 detects a position and/or angle of its associated actuator 80, 82, and/or 84 and feeds the sensed position/angle to controller 76. Controller 76 uses the outputs from sensors 88 as inputs into a closed-loop feedback system for controlling the motion of the actuators 80, 82, and 84, and the components of patient support apparatus 20 moved by these actuators.

In some embodiments, sensors 88*a*-*d* (FIG. 3) are Hall-effect sensors or encoders that output a pulse with each rotation, or with each fraction of a rotation, of the motors incorporated into actuators 80*a*, 80*b*, 82, and 84. In other embodiments, sensors 88*a*-*d* may be potentiometers that output a voltage whose amplitude varies with the amount of extension and retraction of the actuators 80*a*, 80*b*, 82, and 84. In still other embodiments, sensors 88*a*-*d* may take on other forms. Still further, in some embodiments, multiple sensors 88 may be used for each actuator, and such multiple sensors may take on different forms. For example, in some embodiments, each actuator includes an encoder 88 that measures the amount of rotation of the actuators motor and one or more switches 88 that are tripped when the actuator extends or retracts to certain predetermined limits. By combining the outputs from both the encoders and the switches, controller 76 receives data indicating not only how much the actuators motor has rotated (via the encoder), but also data indicating the absolute position of the actuator when it trips one or more of the switches. By utilizing multiple sensors in this manner, errors that may arise due to skipped or otherwise inaccurate encoder counts can be eliminated when a switch is tripped.

In some embodiments, one or more of the actuators 80*a*, 80*b*, 82, and/or 84 (FIG. 3) are implemented as linear actuators of the types disclosed in commonly assigned U.S. patent application Ser. No. 15/449,277 filed Mar. 3, 2017, by inventors Aaron Furman et al. and entitled PATIENT SUPPORT APPARATUS WITH ACTUATOR FEEDBACK, the complete disclosure of which is incorporated herein by reference. More specifically, in some embodiments, one or more of the actuators 80*a*, 80*b*, 82, and/or 84 are implemented as linear actuators that are the same as, or similar to, the linear actuators 34 disclosed in the aforementioned '277 application. Further, in some embodiments, one or more of the sensors 88*a*, 88*b*, 88*c*, and 88*d* are implemented as encoders that are the same as, or similar to, the encoders 80 disclosed in the aforementioned '277 application. Still further, in some embodiments, one or more additional sensors 88 are included for each actuator 80*a*, 80*b*, 82, and/or 84 that are the same as, or similar to, the position switches 78 and/or power switches 94 disclosed in the aforementioned application.

However actuators 80*a*, 80*b*, 82, and 84 and sensors 88*a*-*d* are configured and/or implemented in a particular embodiment, sensors 88 provide data to controller 76 that enables controller 76 to determine the current position and/or angle of actuators 80, 82, and 84, and/or the current position and/or angle of the components that are moved by these actuators (e.g. the current position and/or angle of litter frame 28, Fowler section 40, and the gatch (not labeled)). As will be discussed in greater detail below, controller 76 utilizes this data in order to determine when to stop movement of one or more of the actuators 80*a*, 80*b*, 82, and/or 84 in accordance with one or more motion limit messages received by patient support apparatus 20. Such movement stopping overrides the signals coming from the corresponding motion control 86, thereby preventing a user from moving the corresponding actuator beyond one or more limits.

In addition to actuators 80*a*-*b*, 82, and 84, patient support apparatus 20 further includes memory 78 (FIG. 3). Memory 78, in addition to storing other information, stores at least a first setting 90*a* for each of the actuators 80*a*, 80*b*, 82, and 84. Memory 78 may also store at least one second setting 90*b*. The first setting 90*a* refers to a first limit on the motion of one of the actuators 80*a*, 80*b*, 82, or 84 in a first direction, and the second setting 90*b* refers to an alternative first limit on the motion of that actuator in the same direction. In some embodiments, the first setting corresponds to a default setting and the second setting corresponds to an alternative setting.

For example, first setting 90*a* may refer to a default motion limit for a Fowler angle 92 (FIG. 1) of patient support apparatus 20, such as, but not limited to, thirty degrees, and the second setting 90*b* may refer to an alternative motion limit for a Fowler angle 92 of, say, forty-five degrees. As shown in FIG. 1, the Fowler angle 92 refers to the angle between the plane of the litter frame 28 (or a horizontal plane) and the plane of the Fowler section 40. Thus, in this example, when controller 76 utilizes the first setting 90*a*, a user is prevented from pivoting the Fowler section 40 below thirty degrees, and when controller 76 utilizes the second setting 90*b*, a user is prevented from pivoting the Fowler section below forty-five degrees. The user is free, however to pivot the Fowler section 40 over any angle greater than these two angles that is within the range of motion of the Fowler section (i.e. thirty degrees to the maximum angle, or forty-five degrees to the maximum angle).

It will be understood that, although FIG. 3 illustrates memory 78 as only containing a single first setting 90*a* and a single second setting 90*b*, memory 78 typically includes more than these two settings. More specifically, memory 78 includes at least two first settings 90*a* for each actuator 80*a*, 80*b*, 82, and 84. These two first settings 90*a* define the two ends of the range of motion of the corresponding actuator. Memory 78 may also include one or more second settings 90*b* that serve as one or more alternative ends of the range of motion of the corresponding actuator. In some embodiments, memory 78 does not include any second settings 90*b* until patient support apparatus 20 receives a motion limit message from a remote device 54 that includes one or more second settings. In other embodiments, memory 78 includes one or more second settings 90*b* that are programmed therein during the manufacture of patient support apparatus 20, but which are not utilized until it receives a motion limit message from one or more remote devices 54 instructing it to use one of the second settings 90*b*. In still other embodiments, one or more second settings 90*b* may be transmitted to second memory 117 when patient support apparatus 20 is not powered, and controller 76 is programmed to transfer the second settings 90*b* from second memory 117 to memory 78 when patient support apparatus 20 is powered, as will be discussed in greater detail below.

Table 1 below identifies an illustrative set of first and second settings 90*a* and 90*b* that may be present within memory 78 of patient support apparatus 20. The first column (left-most) identifies the four actuators 80a, 80b, 82, and 84 that are present on patient support apparatus 20. The second and third columns identify the downward motion limits on each of these actuators, and the fourth and fifth columns identify the upward motion limits on each of these actuators. Together, the downward motion limit and the upward motion limit on any given actuator defines the range of motion for that particular actuator. As will be discussed in more detail below, controller 76 chooses which settings (90a or 90b) to utilize for limiting movement of a given actuator based on the receipt of a motion limit message from a remote device 54 and/or based upon data stored in second memory 117.

Thus, in the example shown in Table 1, the first lift actuator 80a has a downward limit on its motion of X and an upward limit on its motion of S when controller 76 is utilizing the first settings 90a of first lift actuator 80a. The variable X therefore defines the minimum height to which litter frame 28 may be lowered and the variable S defines the maximum height to which litter frame 28 may be lifted. The variables X and S may refer to a specific value of height 94 (e.g. a specific number of inches, centimeters, etc.) or they may refer to encoder counts that correspond to the respective desired minimum and maximum heights 94 (if sensor(s) 88 includes an encoder), or they may refer to voltages that correspond to the respective desired minimum and maximum heights 94 (if sensor(s) 88 includes a potentiometer).

In the examples shown in Table 1 below, first lift actuator 80a has two second settings 90b associated with it, the first of which defines an alternative minimum height Y and the second of which defines an alternative maximum height T. As with variables X and S, the variables Y and T may refer to height values, encoder values, potentiometer values, or some other values used to measure the height 94 of litter frame 28 at the location of first actuator 80a.

TABLE 1

| | Motion Limit Settings 90a, 90b | | | |
|---|---|---|---|---|
| | Downward Motion Limits | | Upward Motion Limits | |
| Actuator | 1$^{st}$ setting (90a) | 2$^{nd}$ setting (90b) | 1$^{st}$ setting (90a) | 2$^{nd}$ setting (90b) |
| 1$^{st}$ Lift 80a | X | Y | S | T |
| 2$^{nd}$ Lift 80b | X | Y | S | T |
| Fowler 82 | A | B | C | C |
| Gatch 84 | P | P | Q | R |

As is also shown in Table 1, second lift actuator 80b includes the same first and second settings 90a and 90b for both its upward motion limits and its downward motion limits. This is typical, but not necessary, for patient support apparatus 20. That is, it is often desirable for lift actuators 80a and 80b to extend and retract the same amount in order to ensure that litter frame 28 stays relatively level. It will be understood, however, that second lift actuator 80b may include one or more first and/or second settings 90a and/or 90b that are different from the corresponding settings 90a and/or 90b of first lift actuator 80a.

In the example of Table 1, Fowler actuator 82 is shown to have, according to its first settings 90a, a downward limit on its motion of A and an upward limit on its motion of C. It is also shown to have, according to its second settings 90b, a downward limit on its motion of B and an upward limit on its motion of C. Thus, it can be seen from this example that second setting 90b may be the same as the first setting 90a for one of the limits to an actuator's range of motion (e.g. the upward range of motion of Fowler actuator 82 is the same for both first and second settings 90a and 90b). It will be understood that this equal upper motion limit for the Fowler actuator 82 has been selected as merely an example, and that Fowler actuator 82 may utilize different upward limits on its range of motion (e.g. second setting 90b for its upward movement may be different from first setting 90a for its upward movement).

Gatch actuator 84 is shown in Table 1 to have the same first and second settings 90a and 90b for its downward motion. This is common for gatch actuators because gatch actuators typically all have a lower limit that defines a horizontal orientation for both an upper leg (or thigh section) of support deck 30 and a lower leg (or foot section) of support deck 30, and it is desirable to always be able to lower the joint between these two sections to a lower most position in which the upper and lower leg portions of the support deck 30 are flat. In other words, it is desirable to be able to control the gatch actuator 84 such that its corresponding support deck sections can be moved to a flat orientation, thereby allowing the patient to lie with his or her legs resting straight on mattress 38.

As was noted previously, in some embodiments of patient support apparatus 20, memory 78 contains only a pair of first settings 90a (and no second settings 90b) for each of the actuators 80a, 80b, 82, and 84 when the patient support apparatus is initially installed in a healthcare facility. After installation, controller 76 uses those first settings 90a to determine when to stop the motion of the actuators 80a, 80b, 82, and 84. Controller 76 continues to use those first settings 90a for controlling the range of motion of the actuators 80a, 80b, 82, and 84 until it receives a motion limit message that contains at least one second settings 90b for at least one of the actuators 80a, 80b, 82, or 84. After receiving the motion limit message, controller 76 uses the second setting 90b contained within the message for controlling movement of the corresponding actuator. Thus, for example, controller 76 may initially allow a user to lower litter frame 28 to a minimum height 94 of fifteen inches above the ground, but after receiving a motion limit message, may change that such that the user can lower the support deck 30 to a minimum height 94 of ten inches above the ground. The maximum height of the support deck 30 may or may not change, depending upon the contents of the motion limit message.

It will be appreciated by those skilled in the art that, although Table 1 illustrates only first and second settings 90a and 90b, it is possible for patient support apparatuses 20 to receive and/or store additional settings beyond these two. That is, patient support apparatuses 20 are configured to receive and implement an unlimited number of new motion limit messages, each containing at least one new motion setting. As a result, the ranges of motion of one or more components of patient support apparatus 20 can be adjusted as many times as desired. It will also be appreciated that controller 76 may be configured to erase one or more of the first settings 90a whenever it receives a new, second setting 90b, and/or erase a previous second setting 90b if it receives a third setting (e.g. 90c, not shown) after having the second setting 90b. In other words, controller 76 may be programmed to erase all settings 90a, 90b or 90c that are not currently in use for defining a range of motion of an actuator. Alternatively, controller 76 may be configured to retain the settings 90a, 90b, etc. and switch to actively using one based on the latest motion limit message received from off-board device 54a, b, or c.

Table 2 below illustrates an example of a motion limit message 96 that may be sent to patient support apparatus 20 from one or more of off-board devices 54a, b, and/or c. Motion limit message 96 includes a plurality of fields 98 that identify various components of the message 96. In the example shown, motion limit message 96 includes a header field 98a, a patient support apparatus identifier field 98b, an actuator ID 98c, an upper or lower limit identifier field 98d, a limit value field 98e, a units field 98f, and a security field 98g.

TABLE 2

| Motion Limit Message 96 | | | | | | |
|---|---|---|---|---|---|---|
| Header 98a (98a) | PSA 20 ID (98b) | Actuator ID (98c) | Upper/Lower (98d) | Limit (98e) | Units (98f) | Security (98g) |

The header field 98a identifies the motion limit message 96 as a motion limit message. That is, different types of messages may be sent to patient support apparatus 20 and header field 98a distinguishes the motion limit message 96 from other types of messages. The patient support apparatus identifier field 98b identifies the particular patient support apparatus 20 that the motion limit message 96 is addressed to. In some embodiments, this field may be omitted, particularly if the motion limit message 96 is encapsulated within a lower level message protocol (e.g. an Ethernet frame, an IP packet, etc.) that includes an identifier for the specific patient support apparatus 20 to which the message 96 is intended (e.g. a MAC address or IP address of the patient support apparatus 20).

The actuator ID field 98c identifies which of the actuators 80a, 80b, 82, or 84 the motion limit message 96 is intended for. Specifically, it identifies which of the actuators the setting value contained within limit field 98e applies to. The upper/lower field 98d identifies which of the limits (upper or lower) the setting value contained within the limit field 98e corresponds to. In other words, field 98d tells controller 76 whether the value within field 98e pertains to the upper limit of an actuator or a lower limit of the actuator. The limit field 98e identifies the actual limit value that controller 76 is to use to limit motion of the actuator. The limit field 98e therefore contains the value of second setting 90b (or, if multiple motion limit messages are sent, the value of third, fourth, fifth, etc. settings 90c, 90d, 90e, etc.). As noted previously, the limit value may be specified in units of distance, encoder counts, voltages, or otherwise. Unit field 98f tells controller 76 which units the setting value contained within limit field 98e is written in (e.g. inches, centimeters, encoder counts, volts, millivolts, etc.). Finally, security field 98g includes data that is used in any suitable manner to ensure that the motion limit message 96 is a valid message 96 received from an authorized remote device 54a, b, and/or c.

It will be understood that motion limit message 96 may include additional fields 98 beyond those illustrated. For example, motion limit message 96 may include additional data specifying when and under what conditions the motion limit message data is to be implemented. For example, and as will be discussed in more detail below, some motion limits received by patient support apparatus 20 are only implemented when a particular lockout control 100 (FIG. 3) is activated on patient support apparatus 20 (and when a user subsequently activates the corresponding motion control 86), while other motion limits are implemented by patient support apparatus 20 without requiring a lockout control 100 to be activated, thereby limiting motion of the corresponding actuator any time a user activates the corresponding motion control 86.

It will be understood that motion limit message 96 may include fewer fields 98 than those illustrated in Table 1. For example, in some embodiments, all motion limit values are specified in a uniform set of units so that unit field 98f may be omitted. Alternatively, or additionally, controller 76 may be programmed to decipher whether the value of the motion limit contained within field 98e is an upper or a lower limit based upon the value sent, thereby enabling the motion limit message 96 to eliminate the upper/lower field 98d. Still other fields may be omitted or combined.

It will further be understood that the order of the fields 98 within a message 96 is not material, and that an individual motion limit message 96 may include more motion limit data than only data for a single endpoint of one end of a range of motion of a single actuator. In other words, a single motion limit message 96 may include a pair (or more) of settings (both contained within field 98e, or alternatively each having their own limit field 98e) that define both the first and second endpoints for one or more actuators' ranges of acceptable motion. Still other data may be added to the motion limit message 96.

Finally, it will be understood that motion limit message 96 may be modified to simply contain an instruction to controller 76 to utilize an alternative setting 90b (or 90c or 90d etc.) that is already stored on-board patient support apparatus 20 in memory 78. That is, in some embodiments, patient support apparatus 20 includes a plurality of settings 90a and 90b (or more) that are pre-stored in memory 78 and controller 76 utilizes the default ones of those settings (e.g. 90a) until instructed otherwise by receipt of a motion limit message 96. In such cases, the motion limit message 96 need not specify the limits of the motion, but instead can identify a memory location corresponding to the one or more pre-stored alternative settings 90b, 90c, etc., or otherwise instruct controller 76 to utilize the alternative setting 90b, 90c, etc.

Controller 76 is in communication with all of the user interfaces 42a, 42b, and 42c, as shown in FIG. 3. As noted, footboard user interface 42a includes a touchscreen display 46 and one or more motion controls 86 and one or more lockout controls 100. Both motion controls 86 and lockout controls 100 may be implemented as dedicated controls 48 (FIG. 1), or they may be implemented as icons on a particular screen that is displayed on touchscreen display 46. For purposes of the following written description of footboard user interface 42a, controls 86 and 100 will primarily be described as touchscreen implemented controls, although it will be understood that this is merely done for convenience, and that such controls may alternatively be implemented as touch sensitive dedicated controls 48. Such dedicated controls 48, when included, may be physically implemented in a variety of different manners, such as, but not limited to, as capacitive sensors positioned adjacent display 46 that capacitively detect when a user presses them, or as one or more buttons, switches, or other types of force or touch-sensitive devices.

Figure 4:
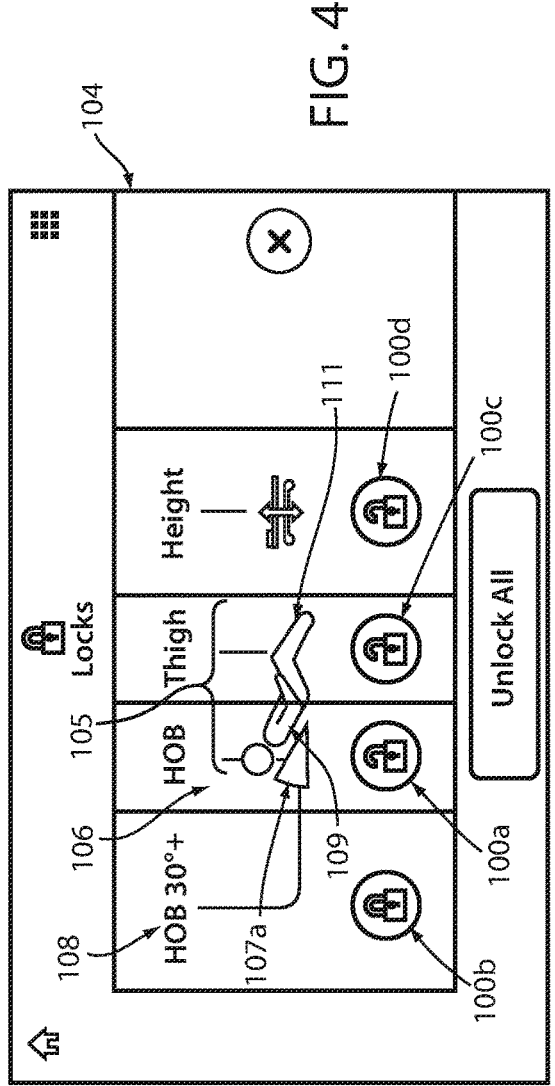
FIG. 4 is an illustrative screen shot of a first lockout control screen displayable on the display of the patient support apparatus of FIG. 1 when a partial lockout for a head of bed angle control has been set to a first configuration.

FIG. 4 illustrates in greater detail a lockout control screen 104 that is displayed by controller 76 on touchscreen display 46 in response to a user navigating to this screen. That is, controller 76 displays a plurality of other control screens, as least one of which includes a control for causing controller 76 to display lockout control screen 104 on display 46. Lockout control screen 104 is used by a user when he or she wishes to prevent a patient (or caregiver) from being able to partially or wholly use one or more of the motion controls of user interfaces 42 to move patient support apparatus 20 in certain manners. Typically, lockout screen 104 is used when a caregiver wants to prevent a patient from moving one or more components of patient support apparatus 20. By selecting one or more lockout functions displayed on screen 104, the caregiver is able to prevent the patient associated user interfaces 42*b* (and in some embodiments, all user interfaces 42) from moving the patient support apparatus components that have been locked out, as will now be discussed in more detail.

Figure 6:
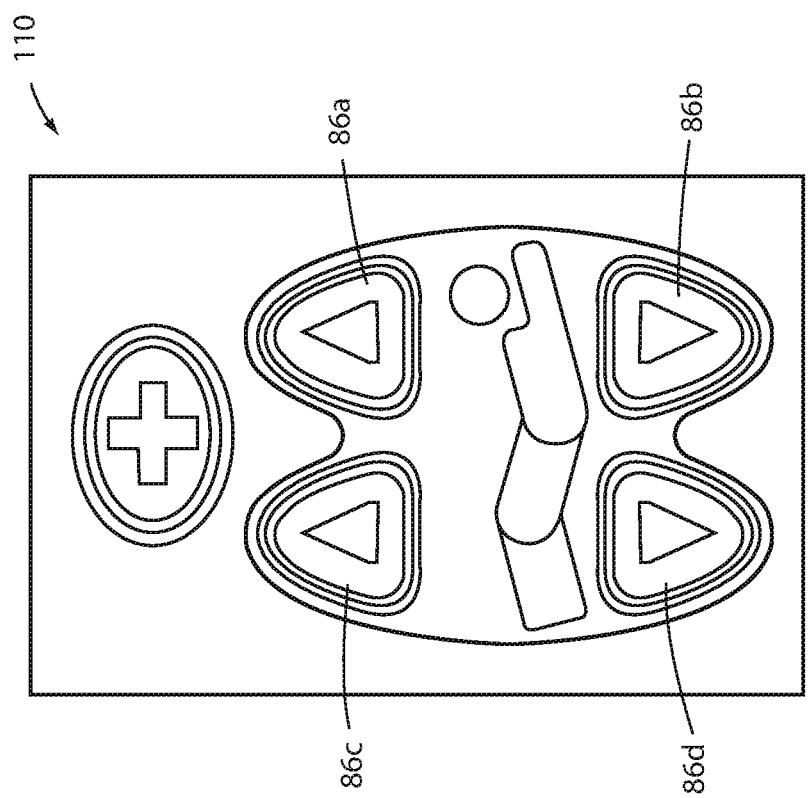
FIG. 6 is a plan view of an illustrative patient user interface of the patient support apparatus of FIG. 1 showing a plurality of motion controls implemented as physical buttons.
Figure 7:
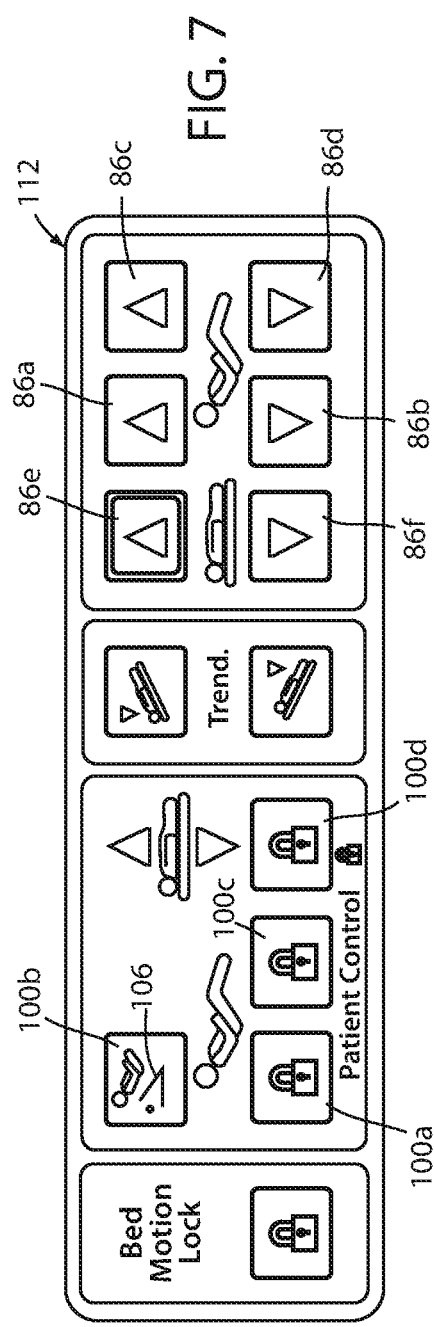
FIG. 7 is a plan view of an alternative caregiver user interface that may be incorporated into an alternative embodiment of the patient support apparatus of FIG. 1 wherein the user interface shows a head of bed angle lockout control and other controls implemented as physical buttons.

FIG. 4 illustrates a complete Fowler lockout control 100*a*, a partial Fowler lockout control 100*b*, a thigh or gatch lockout control 100*c*, and a height lockout control 100*d*. The complete Fowler lockout control 100*a*, when activated by a user (such as by pressing the corresponding lock icon on screen 104) prevents a user from pivoting Fowler section 40. This means that if a patient presses on a motion control 86 that normally (i.e. when not locked out) pivots Fowler section 40, controller 76 overrides and/or ignores the signal from the motion control 86 and does not activate the Fowler actuator 82. Examples of such motion controls 86 are shown in FIGS. 6 and 7 (e.g. Fowler motion controls 86*a* and 86*b*), as well as FIG. 11. In at least some embodiments, the activation of full Fowler lockout 100*a* locks out the Fowler motion controls 86*a* and 86*b* on all of the user interfaces 42*a*, 42*b*, and 42*c* of patient support apparatus 20, while in other embodiments, the activation of full Fowler lockout control 100*a* only locks out the Fowler motion controls on one or two sets of the user interfaces 42, but not all of them (e.g. user interfaces 42*b* is locked, but not user interfaces 42*a* and 42*c*; or user interfaces 42*b* and 42*c* are locked, but not user interface 42*a*, etc.)

The partial Fowler lockout 100*b*, when activated, locks out motion of the Fowler section 40 that would otherwise cause the Fowler angle 92 to decrease below a threshold angle. In the specific example shown in FIG. 4, the threshold angle is thirty degrees, which is indicated by identifier 108. Consequently, when a user activates partial fowler lockout 100*b*, a patient (or caregiver) can pivot the Fowler section 40 using a corresponding motion control 86 so long as he or she does not try to pivot the Fowler section 40 below thirty degrees. If he or she attempts to pivot the Fowler section below thirty degrees, controller 76 stops further movement of the Fowler actuator 82. In other words, whenever a person pivots Fowler section 40 downward and partial Fowler lockout 100*b* is activated, controller 76 stops the downward movement at thirty degrees (or earlier if the user lifts his or her finger from the corresponding Fowler pivot control 86 prior to Fowler section 40 reaching thirty-degrees). In some embodiments, partial Fowler lockout 100*b* stops the motion at the designated threshold (e.g. thirty-degrees) and thereby permits movement to the threshold angle, while in other embodiments partial Fowler lockout permits movement up to, but not inclusive of, the threshold angle (e.g. stops Fowler movement at just above thirty-degrees). Partial Fowler lockout 100*b* is useful in situations where a patient may be on a respirator and it is desirable to keep the patient's torso elevated beyond a certain angle in order to reduce the likelihood of ventilator associated pneumonia. Partial Fowler lockout 100*b* may be used in other situations as well.

In some embodiments, partial Fowler lockout 100*b* and complete Fowler lockout 100*a* are configured to toggle between each other. In other words, if a user presses partial lockout control 100*b* while full lockout control 100*a* is active, controller 76 shuts off the full lockout control 100*a* and implements the partial lockout feature of partial lockout control 100*b*. Conversely, if the user presses full lockout control 100*a* while partial lockout control 100*b* is active, controller 76 shuts off the partial lockout control 100*b* and activates the full lockout feature of full lockout control 100*a*. If a user desires to cancel either full Fowler lockout 100*a* or partial Fowler lockout 100*b*, he or she simply presses the control 100*a* or 100*b* that is currently active and controller 76 terminates the activation of that lockout feature. Thus, controls 100*a* and 100*b* toggle on and off when an individual one of them is pressed successively, and toggle between each other when one of them is first pressed and the other of them is subsequently pressed. Other manners for activating and deactivating these controls 100*a* and/or 100*b* may, of course, be used.

Thigh or gatch lockout control 100*c* locks out motion of the gatch actuator when it is activated. Thus, when a user activates a motion control 86 that normally controls gatch actuator 84 (e.g. motion controls 86*c* and 86*d* of FIGS. 6, 7, and 11) and lockout control 100*c* has been activated, controller 76 does not activate the gatch actuator 84. This prevents the patent from adjusting how the patient support apparatus 20 supports his or her legs.

Height lockout control 100*d* locks out control of the lift actuators 80*a* and 80*b*. As a result, when a patient or caregiver attempts to raise or lower litter frame 28 with respect to base 22 by activating a corresponding lift control 86 (e.g. control 86*f* of FIG. 11), controller 76 ignores those actions and does not power actuators 80*a* or 80*b*.

When neither complete Fowler lockout control 100*a* nor partial Fowler lockout control 100*b* are pressed (i.e. activated) by a user, controller 76 responds to a user pressing on Fowler motion control 86*a* or 86*b* by activating the Fowler actuator 82 in the corresponding direction and the user is free to move the Fowler section 40 to any desired orientation. If the user does not activate complete Fowler lockout control 100*a*, but instead only activates partial Fowler lockout control 100*b*, controller 76 responds to the user pressing on Fowler motion control 86*a* (the up control) by activating Fowler actuator 82 and moving Fowler section 40 upwards, and controller 76 responds to the user pressing on Fowler motion control 86*b* (the down control) by activating actuator 82 and moving Fowler section 40 downwards, but only until the Fowler section 40 reaches the angular limit imposed by partial Fowler lockout control 100*b* (e.g. thirty degrees in the example of FIG. 4 and forty-five degrees in the example of FIG. 5). If neither lockout control 100*a* nor 100*b* is pressed, then the user is, of course, free to utilize the motion controls 86*a* and 86*b* to move the Fowler section over its entire range of motion, which may vary from embodiment to embodiment, but is generally in the range of about zero degrees to about ninety degrees.

In many conventional patient support apparatuses the minimum Fowler angle 92 that controller 76 enforces when partial Fowler lockout 100*b* is activated is set during the manufacture of the patient support apparatus and cannot be changed. However, due to differing practices of different healthcare facilities, as well as ongoing medical research, it may be desirable for this minimum Fowler angle 92 to be adjustable by authorized representatives of a healthcare facility, and patient support apparatus 20 allows this minimum Fowler angle 92 to be adjusted. Specifically, patient support apparatus 20 is adapted to change this minimum Fowler angle 92 in response to a motion limit message 96 containing data for a new minimum Fowler angle.

Figure 5:
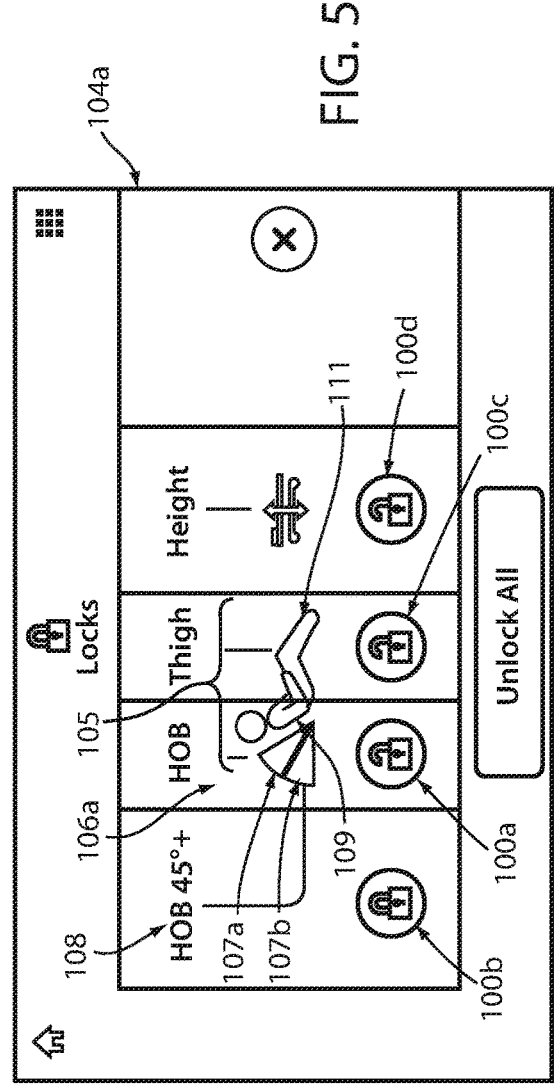
FIG. 5 is an illustrative screen shot of a second lockout control screen displayable in lieu of the first lockout control screen of FIG. 4 when the partial lockout for the head of bed angle control has been set to a second configuration.

FIG. 5 illustrates a modified lockout control screen 104*a* that is displayed in response to patient support apparatus 20 having had at least one of the acceptable ranges of motion of its actuators 80*a*, 80*b*, 82, and/or 84 reconfigured via a motion limit message 96. More specifically, modified lockout screen 104*a* is displayed on touchscreen 46 after patient support apparatus 20 has received a motion limit message 96 containing data for a new minimum Fowler angle 92. This change is shown by identifier 108 which indicates a minimum threshold of forty-five degrees, and which is different from the identifier 108 of FIG. 4, which indicates a thirty degree minimum threshold. This change is the result of patient support apparatus 20 having received a motion limit message 96 that specifies forty-five degrees as the new minimum Fowler angle for partial Fowler lockout 100*b*. In other words, patient support apparatus 20 displays modified lockout screen 104*a* after having received a motion limit message 96 containing a second setting 90*b* specifying forty-five degrees for the lower limit of Fowler actuator 82. As a result of receiving this motion limit message 96, controller 76 changes to preventing the Fowler angle 92 from decreasing below forty-five degrees when lockout 100*b* is activated.

Although FIG. 5 has been described above as referring to a modified lockout screen 104*a* that is only displayed after receiving a motion limit message 96 containing a new minimum Fowler angle 92, it will be understood that the screen 104*a* of FIG. 5 may be the original screen displayed by controller 76 and screen 104 of FIG. 4 may be the modified screen that is only displayed in response to a motion limit message 96 containing a new minimum Fowler angle 92. That is, patient support apparatus 20 may be initially configured to prevent movement of Fowler section 40 below forty five degrees when partial lockout 100*b* is activated, and then be switched to another angular minimum (e.g. the thirty degrees of FIG. 4) in response to a motion limit message 96. It will further be understood that both the initial and subsequent numeric lockout values of FIGS. 4 and 5 are but only two examples of values from amongst many different initial and subsequent values that may be implemented on patient support apparatus 20. Indeed, in some embodiments, an authorized administrator is free to set the minimum Fowler angle enforced in response to a user activating lockout control 100*b* to any value he or she chooses. The authorized administrator can therefore customize the minimum angle enforced by partial lockout control 100*b* on all, or a selected portion, of the patient support apparatuses 20 within a given healthcare facility. In some embodiments, this customization is able to be accomplished at a centralized location, such as at a computer terminal in communication with patient support apparatus server 54*a*.

In some embodiments, when partial Fowler angle lockout 100*b* is activated and the current Fowler angle 92 is less than the minimum threshold, controller 76 is configured to automatically raise the Fowler section 40 until its angle matches the minimum Fowler angle. In other embodiments, controller 76 does not automatically activate Fowler actuator 82 but instead issues an alert (audio and/or visual, and local and/or remote) that indicates to the user that the current Fowler angle 92 is less than the desired minimum Fowler angle and leaves it to the user to raise the Fowler angle 92 up to the minimum (or above). In still other embodiments, controller 76 is configured to gray out, or otherwise inactivate, partial Fowler lockout 100*b* whenever the current angle of the Fowler section 40 is less than the threshold angle associated with partial Fowler lockout 100*b*. Thus, for example, if partial Fowler lockout 100*b* is set to a minimum threshold of thirty-degrees, controller 76 grays out lockout 100*b*, or otherwise inactivates it, whenever the angle of Fowler section 40 is less than thirty-degrees. In this example, controller 76 ceases to display the partial lockout 100*b* in a grayed out fashion, or otherwise activates partial lockout 100*b*, whenever the angle of the Fowler section 40 is moved to more than thirty-degrees. In addition to graying out lockout control 100*b* when it is not able to be activated, controller 76 may be configured to gray out one or more other aspects of the display screen, such as, but not limited to, the text indicating the minimum angular threshold of the partial Fowler lockout 100*b* (e.g. "HOB 30°+" in FIG. 4). The graying out of lockout 100*b* (or any of the other lockout controls 100*a*, *c*, and/or *d*) may include graying out a perimeter of the circle corresponding to lockout control 100*b*, the lock icon inside the circle, both the perimeter and lock icon, and/or the entire circle including the perimeter, lock icon, and interior area of the circle. Still further, such graying out may include graying out of the area inside of the rectangular section of screen 104*a* associated with lockout control 100*b*.

Controller 76 is configured to make no automatic movements of Fowler section 40 if it receives a motion limit message 96 specifying a new minimum Fowler angle 92 and the partial Fowler lockout 100*b* is currently active. Instead, controller 76 is configured to issue an alert (audio and/or visual, and local and/or remote) indicating that the current Fowler angle 92 is less than the new desired minimum Fowler angle 92, and/or to gray out, or otherwise inactivate, partial Fowler lockout control 100*b*. Controller 76 is further programmed to automatically implement the new minimum Fowler angle 92 after the Fowler section 40 is raised to, or above, the new minimum Fowler angle. As a result, if the partial Fowler lockout 100*b* is activated and patient support apparatus 20 receives a new minimum Fowler angle 92 that is greater than the current Fowler angle 92, controller 76 does the following: (1) issues an alert and/or grays out (or otherwise inactivates partial lockout control 100*b*); (2) prevents the Fowler section 40 from being lowered any further; (3) allows the Fowler section 40 to be raised to and beyond, the new minimum Fowler angle 92; and (4) thereafter prevents the Fowler section 40 from being lowered past the new minimum Fowler angle 92. Controller 76 may also be programmed to prevent any lowering of the Fowler section 40 while the current Fowler angle 92 is less than the new minimum Fowler angle 92. For example, if the new minimum Fowler angle 92 is forty-five degrees and the current angle is thirty-five degrees, the patient will not be able to lower the Fowler section 40 but will be able to raise the Fowler section 40. However, if the patient raises to the Fowler angle to, say, forty-degrees, which is still less than the new minimum angle of forty-five degrees, controller 76 prevents the Fowler from being lowered back to its original thirty-five degrees. Thus, controller 76 continually adjusts upward the minimum Fowler angle 92 as the Fowler section is raised until it reaches the new minimum Fowler angle specified in the latest motion limit message 96.

It will be understood that the new motion limit settings contained within a motion limit message 96—such as, but not limited to, the new minimum Fowler angle 92 just described—cannot be changed via the user interfaces 42 of patient support apparatus 20 in some embodiments. That is, a user or caregiver associated with patient support apparatus 20 is not able to navigate through the various screens of touchscreen display 46 to a page or screen having a control that enables him or her to adjust the minimum Fowler angle 92. Nor can a user use any of the dedicated controls 48 change the new motion limits defined in any of the motion limit messages 96. Instead, these motion limits are only changeable by authorized personnel who have access to one or more of the remote devices 54 (e.g. local server 54*a*, remote server 54*b*, or portable electronic device 54*c*) with a corresponding motion limit software application installed thereon.

Figure 12:
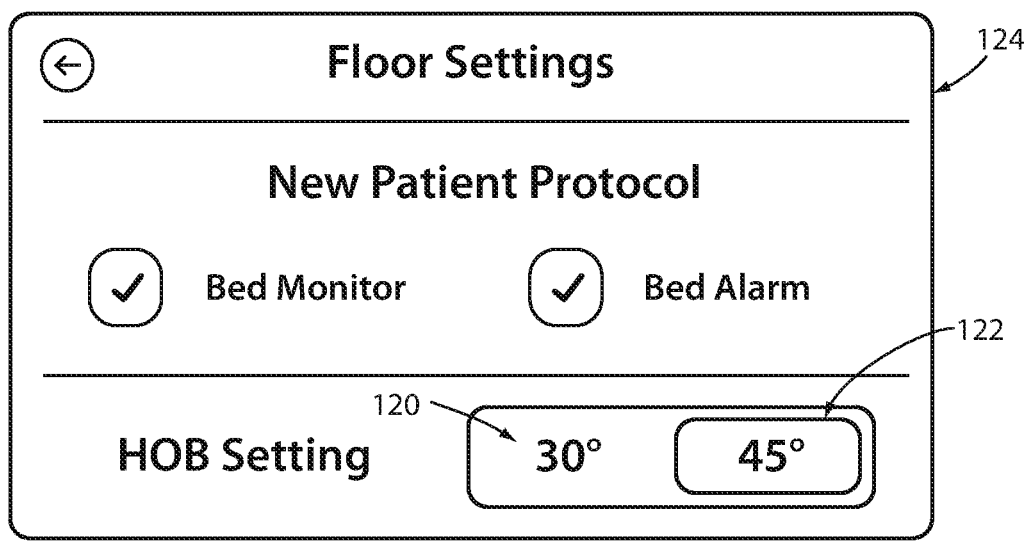
FIG. 12 is an illustrative screen shot of a settings screen displayable on some embodiments of the patient support apparatus of FIG. 1.

In other alternative embodiments, controller 76 may be configured to display a settings screen, such as setting screen 124 of FIG. 12, on display 46 that includes one or more controls 20 for allowing the caregiver to customize the minimum angular threshold of partial Fowler lockout control 100*b*, and/or for allowing the caregiver to customize any of the other customizable settings discussed herein (e.g. minimum height of litter frame 28, etc.). FIG. 12 illustrates one example of such a settings screen for customizing the minimum angular threshold of the partial Fowler lockout control 100*b*. As shown therein, settings screen 124 includes a first Fowler angle lockout setting control 120 and a second Fowler angle lockout setting control 122. In this particular embodiment, first control 120 corresponds to a minimum Fowler angle of thirty-degrees, while second control 122 corresponds to a minimum Fowler angle of forty-five degrees. Other angular thresholds may be included, and in some embodiments, controller 76 is adapted to display more than two options. Indeed, in some embodiments, a numeric input function is included that enables a user to manually set the minimum angle to any desired numeric value. In the embodiment of FIG. 12, if the user selects first control 120, then the user interface sends controller 76 a motion limit message that prevents movement of Fowler section 40 below thirty-degrees when partial lockout 100*b* is activated, and if the user selects second control 122, then the user interface sends controller 76 a motion limit message that prevents movement of the Fowler section 40 below forty-five degrees when partial lockout 100*b* is activated. Further, in some embodiments, if the user selects first control 120, controller 76 is configured to display first lockout screen 104 of FIG. 4, and if the user selects second control 122, controller 76 is configured to display second lockout screen 104*a* of FIG. 5. Still further, in at least one other embodiment, if a user selects first control 120, controller 76 is configured to display third lockout screen 104*b* of FIG. 9, and if the user selects second control 122, controller 76 is configured to display fourth lockout screen 104*c* of FIG. 10.

In many embodiments of patient support apparatus 20 that do not allow a caregiver to select a minimum Fowler angle (e.g. those embodiments that do not include a settings screen like screen 124 of FIG. 12), access to the remote devices 54 is restricted to authorized personnel, such as one or more administrators of the healthcare facility. In order to send a new motion limit message 96, the authorized user must log into the corresponding motion limit software application running on the remote device 54 and instruct the software application to send a new motion limit message 96 to one or more of the patient support apparatuses 20 within the healthcare facility. Access to this software application may be restricted via passwords and/or other means. The new motion limit messages 96 are used by healthcare administrators to custom-tailor different aspects of the motion of patient support apparatus 20 to match the preferences of the healthcare facility. The caregivers that actually use the patient support apparatus 20 therefore do not need to concern themselves with the specific value of the minimum Fowler angle 92 that controller 76 uses when partial Fowler lockout 100*b* is activated. Instead, they can simply press the lockout 100*b* when appropriate and know that the patient support apparatus 20 has implemented the minimum Fowler angle preferred by the administrators of the healthcare facility. Similarly, the caregivers do not need to concern themselves with how low the litter frame 28 should be moved to in order to reduce fall risks—he or she can simply activate the litter lowering motion control 86 until the litter frame 28 reaches its minimum height.

As can be seen from FIGS. 4 and 5, controller 76 is configured to display on screens 104 and 104*a* a graphical representation 106. Graphical representation 106 is shown next to Fowler lockout 100*a* and partial Fowler lockout 100*b*. Graphical representation 106 includes an icon 105 representing a stylized drawing of a patient's body that is comprised of a head and torso section 109 and a leg section 111. Graphical representation 106 also includes a wedge 107*a* that, as discussed below, is only displayed when partial Fowler lockout 100*b* is activated. Patient icon 105 is shown in FIG. 4 lying against wedge shape 107*a* at a particular angle. Wedge section 107*a* represents a range of motion that is forbidden by Fowler section 40 when partial Fowler lockout 100*b* is activated. Thus, in the example of FIG. 4, wedge 107*a* subtends an angle equal to, or approximately equal to, thirty degrees. Controller 76 is configured to adjust the angle subtended by wedge 107*a* in response to changes in the minimum threshold angle of partial lockout control 100*b*. In some embodiments, controller 76 simply increases the size of wedge 107*a* if the minimum Fowler angle is increased and decreases the size of the wedge 107*a* if the minimum fowler angle is decreased.

In the embodiment of FIGS. 4 and 5, controller 76 is specifically configured to add a second wedge 107*b* in response to a motion limit message that increases the minimum Fowler angle of partial lockout 100*b*. As can be seen in FIG. 4, graphical representation 106 shows both a first wedge 107*a* and a second wedge 107*b* that together subtend an angle equal to, or approximately equal to, forty-five degrees (the new minimum Fowler angle of partial lockout 100*b*). Thus, from a comparison of FIG. 4 and FIG. 5, it can be seen that controller 76 adjusts the composition of graphical representation 106 in response to different minimum Fowler angle settings. More specifically, the different ways of displaying graphical representation 106 are the result of controller 76 being programmed to adjust the graphical representation 106 based on the content of a motion limit message 96. In the embodiment shown in FIGS. 4 and 5, controller 76 changes the number of wedges 107 displayed to generally indicate the range of motion of the Fowler section 40 that is prohibited when the partial Fowler lockout 100*b* is activated. That is, the angle subtended by the longest two sides of the single wedge 107*a* (or the combined angle subtended by both wedges 107*a* and 107*b*) is equal to the minimum angle below which the Fowler section 40 cannot be pivoted (when the partial lockout 100*b* is activated). As will be discussed more below with respect to FIGS. 9 and 10, the meaning of these wedges can be modified to refer to the permitted range of motion, rather than the restricted range of motion, in alternative embodiments.

Controller 76 may be configured to change graphical representation 106 in a variety of different manners. For example, in at least one embodiment, whenever a user activates full Fowler lockout 100*a*, partial Fowler lockout 100*b*, gatch lockout 100*c*, or lift lockout 100*d*, controller 76 is configured to change the color of the corresponding icon. For example, in at least one embodiment, if the user activates full or partial Fowler lockout 100*a* or 100*b*, controller 76 changes the color of head and torso section 109; if the user activates gatch lockout 100*c*, controller 76 changes the color of leg section 111, and if the user activates lift lockout 100d, controller 76 changes the color of the corresponding lift icon (not labeled). Controller 76 may further be configured to change the color of the controls 100a, 100b, 100c, and/or 100d themselves in response to the activation and deactivation of these controls, either in addition to, or in lieu of, the changes to the color of graphical representation 106. Such changing of the color of the controls may include changing the color of a perimeter of a circle surrounding the particular control 100a, b, c, and/or d that is pressed, changing the color of the lock icon (not labeled) inside of the circle of the particular control 100a, b, c, and/or d that is pressed by the user, changing the color of any portion of patient icon 105 that is affected by the particular control 100a, b, c, and/or d pressed by the user, changing the color of any text associated with the particular control 100a, b, c, and/or d pressed by the user, and/or changing the color of any other graphic associated with the particular control 100a, b, c, and/or d that is pressed by the user (e.g. any of wedges 107). In some embodiments, the changes in color include changing any one or more of these elements to an orange color when the control 100a, b, c, and/or d is activated, and changing these elements to a different color when the control 100a, b, c, and/or d is not activated. Still other variations are possible.

It will be understood that graphical representations 106 and/or 106a can be changed in a variety of additional or alternative manners from what is shown in FIG. 4 and FIG. 5. It will also be understood that the modifications made by controller 76 to graphical representations 106 and/or 106a that are made in response to receiving a new motion limit message 96 specifying a new minimum Fowler angle 92 can vary from what is represented in FIGS. 4 and 5. Still further, it will be understood that additional changes to graphical representation 106 beyond what is shown in FIGS. 4 and 5 can be made if still other motion limit messages 96 are sent to patient support apparatus 20 defining other minimum Fowler angle values besides thirty and forty-five degrees.

Some specific examples of modifications to screens 104 and/or 104a includes, but are not limited to, the following: controller 76 may change the angle of head and torso section 109 to match the current angle of Fowler section 40 (i.e. dynamically update the head and torso section 109 as the Fowler section 40 moves); controller 76 may change the relative angles of the patient's upper and lower legs in leg section 111 to match the current gatch position of patient support apparatus 20 (i.e. dynamically update the leg section 111 to match the current position of the gatch); controller 76 may change the content of the lift icon (not labeled) in response to changes in the height and/or orientation of litter frame 28; controller 76 may change the size, shape, and/or position of any of, or any portion of, the torso and head section 109 and/or the leg section 111 in response to a motion limit message; controller 76 may change the number, shape, size, and/or color of the wedges 107 in response to a new motion limit message; and/or controller 76 may make any combination of these changes and/or other changes to graphical representations 106 and/or 106a.

Figure 9:
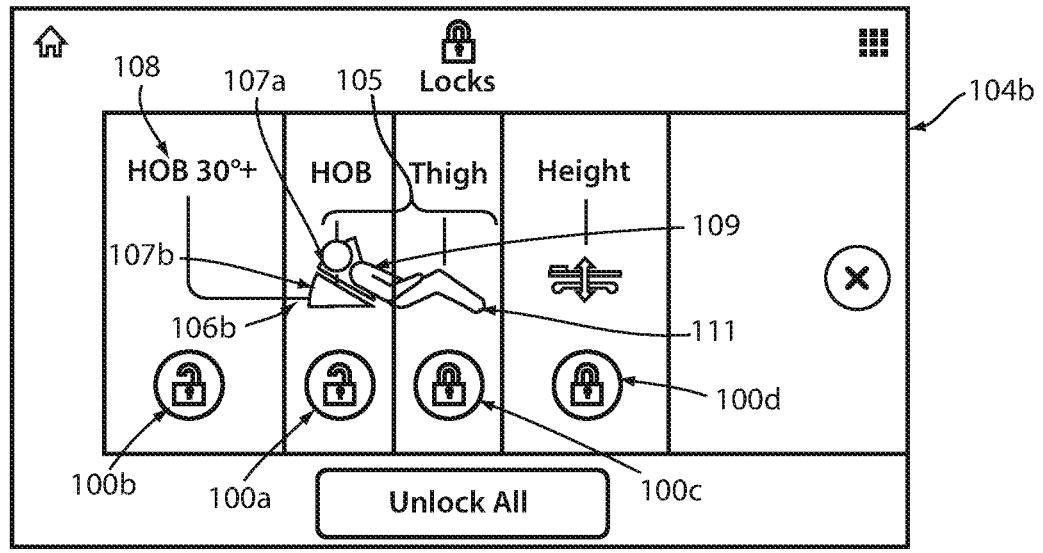
FIG. 9 is an illustrative screen shot of a third lockout control screen displayable on an alternative embodiment of the patient support apparatus of FIG. 1 when a partial lockout for a head of bed angle control has been set to a first configuration.
Figure 10:
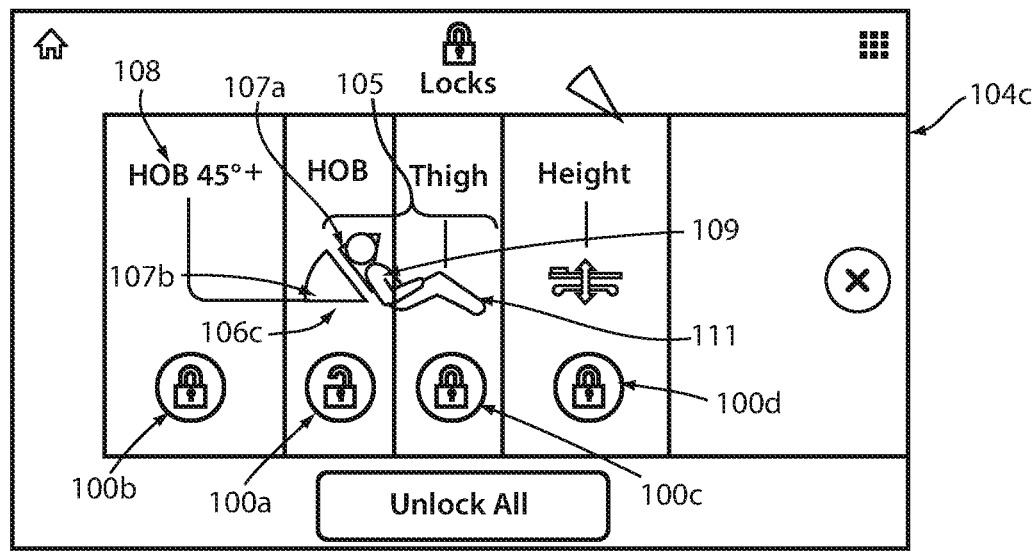
FIG. 10. is illustrative screen shot of a fourth lockout control screen displayable in lieu of the third lockout control screen of FIG. 9 when the partial lockout for the head of bed angle control has been set to a second configuration.

FIGS. 9 and 10 illustrate examples of modified lockout screens 104b and 104c that are displayable on display 46 of a modified embodiment of patient support apparatus 20. Such screens 104b and 104c are examples of alternatives to the screens 104 and 104a of FIGS. 4 and 5. In other words, in some embodiments, patient support apparatus 20 is configured to display either screen 104 or 104a (after a user navigates to that screen), depending upon what angular configuration the partial lockout control 100b has been set to, while in other embodiments, patient support apparatus 20 is configured to display either screen 104b or 104c (after a user navigates to that screen), depending upon what angular configuration the partial lockout control 100b has been set to. Further modifications to any of these four screens may be made if partial lockout control 100b is set to an angular threshold different from the ones shown in these drawings (e.g. something other than thirty or forty-five degrees). Still other modifications to any of these screens 104, 104a, 104b, and/or 104c may be made.

FIG. 9 illustrates a lockout control screen 104b in which neither the full Fowler lockout control 100a nor the partial Fowler lockout control 100b has been activated. In this state, controller 76 is adapted to display a screen 104b which includes a graphical representation 106b having a first wedge 107a and a second wedge 107b. In this particularly embodiment, both first and second wedges 107a and 107b are depicted in the same color (such as, but not limited to, green). The wedges 107a and 107b collectively indicate the angular degree of freedom of Fowler section 40. That is, because neither lockout 100a nor 100b are activated, the user is free to pivot Fowler section 40 throughout its whole range of motion. The wedges 107a and 107b collectively subtend an angle that is equal to, or approximately equal to, the whole range of angular motion of Fowler section 40. Thus, graphical representation 106b, unlike graphical representations 106 and 106a, provides an indication of the degree of freedom of Fowler section 40, rather than a degree of restriction.

If a user decides to activate partial Fowler lockout 100b in the example of FIG. 9, controller 76 is configured to respond to such activation by changing the color of second wedge 107b. In some embodiments, the new color of second wedge 107b is orange, while in other embodiments the new color of second wedge 107b is red. Still other colors are possible. The color change is meant to indicate that second wedge 107b, after partial lockout 100b has been activated, depicts an angular range of motion that is restricted via lockout 100b. That is, second wedge 107b subtends an angle equal to, or approximately equal to, thirty-degrees, which is what patient support apparatus 20 of FIG. 9 is configured to lockout when partial lockout 100b is activated. Thus, the color change of second wedge 107b indicates that Fowler section 40 is no longer able to be pivoted in the angles represented by second wedge 107b when lockout 100b is activated. First wedge 107a remains the same color, thereby indicating that the user is free to pivot Fowler section 40 throughout the upper range of motion (e.g. greater than thirty degrees). If the user activates complete lockout 100a in the example of FIG. 9 (or FIG. 10), controller 76 is configured to change the colors of both wedges 107a and 107b to whatever color has been selected to indicate a prohibited range of motion (e.g. orange, red, grayed out, etc.).

As was described previously, patient support apparatus 20 is adapted to receive a motion limit message 96 from an external source. If the patient support apparatus 20 that is configured to display screen 104b (FIG. 9) receives a motion limit message 96 changing the angular threshold for partial lockout 100b, controller 76 will switch to displaying a screen 104c like that shown in FIG. 10. The particular example of FIG. 10 is for a patient support apparatus 20 that has received a motion limit message specifying a partial lockout threshold of forty-five degrees (which is shown in FIG. 10), but it will be understood that other angular limits may be contained within the motion limit message 96. In response to receiving the new angular threshold, controller 76 modifies the graphical representation 106b of FIG. 9 to graphical representation 106c of FIG. 10. Graphical representation 106c differs from graphical representation 106b in that first wedge 107a of graphical representation 106c is smaller and second wedge 107b of graphical representation 106c is larger. These changes in size correspond to the new angular threshold (i.e. forty-five degrees) that was received in the motion limit message 96. In other words, second wedge 107b is depicted in FIG. 10 to subtend an angle equal to, or approximately equal to, forty-five degrees, and first wedge 107a is depicted to subtend an angle equal to, or approximately equal to, fifteen degrees less than its value in FIG. 9 (due to second wedge 107b increasing by fifteen degrees). In response to this new motion limit message 96, controller 76 is configured to lock out movement of Fowler section 40 to any angles lower than forty-five degrees when partial lockout 100b is activated.

FIG. 10 depicts an example of how controller 76 implements a graphical representation 106c after the user has activated partial lockout 100b (and the patient support apparatus 20 has been instructed to use a forty-five degree angle for the threshold of partial lockout 100b). Controller 76 displays second wedge 107b in a different color than first wedge 107a. More particularly, controller 76 displays second wedge 107b in screen 104c (FIG. 10) in a color different from second wedge 107b (and first wedge 107a) of screen 104b (FIG. 9). This change in color indicates that second wedge 107b in screen 104c depicts the forbidden angular range of motion of Fowler section 40, and the new color of second wedge 107b when partial lockout 100b is activated may be the same color (e.g. orange) that is displayed on screen 104b when partial lockout 100b is activated. Thus, as with screen 104b of FIG. 9, controller 76 changes screen 104c of FIG. 10 in response to the activation of partial lockout control 100b by changing the color of second wedge 107b. Further, in the particular embodiment shown in FIGS. 9 and 10, controller 76 displays head and torso section 109 in the same color (e.g. white) regardless of whether partial Fowler lockout 100b is activated or not. Controller 76 is configured to change the color of head and torso section 109 in response to full Fowler lockout 100a being activated (e.g. such as by changing head and torso section 109 to orange).

Controller 76 displays first wedge 107a in FIG. 10 in the same color as first wedge 107a of FIG. 9 because in both drawings, first wedge 107a subtends an angular range of motion that is permitted. Were a user to activate full lockout 100a from either of the screens 104b or 104c, controller 76 is configured in some embodiments to display both first and second wedges 107a and 107b in a third color, such as a color that matches the background of screen 104b so that wedges 107a and 107b are no longer visible. Alternatively, controller 76 may be configured to display wedges 107a and 107b in a grayed out fashion whenever full lockout 100a is activated in order to indicate that the full range of motion of Fowler section 40 has been locked out. When a user deactivates both full lockout 100a and partial lockout 100b, controller 76 is configured to display both first and second wedges 107a and 107b in the same color as first wedge 107a of FIG. 10 (e.g. green). As with screens 104 and 104a of FIGS. 4 and 5, controller 76 in the embodiment of FIGS. 9 and 10 may be further configured to make any of the additional color and/or graphical representation changes discussed above, such as, but not limited to, changing the color of lockout controls 100a-d in response to their activation and deactivation, changing the angles of head and torso section 109 in response to movement of the Fowler section, changing the angles and/or composition of leg section 111 so that patient icon 105 appears to be sitting up more or less, changing the number, size, and/or shape of the wedges 107, etc.

FIG. 6 illustrates an example of a control panel 110 that may be incorporated into one or both of the user interfaces 42b that are intended to be used by the patient associated with patient support apparatus 20. Control panel 110 includes a plurality of dedicated controls 48. Amongst these dedicated controls 48 is a Fowler raise control 86a, a Fowler lower control 86b, a gatch raise control 86c and a gatch lower control 86d. Unless a corresponding lockout 100 is activated, pressing on any of these motion controls 86 causes the controller 76 to activate the corresponding actuator(s) in the manner corresponding to the particular direction associated with the motion control 86 that has been activated (e.g. pressing Fowler raise control 86a causes controller 76 to activate the Fowler actuator 82 in a manner that raises the Fowler section 40 upwardly, thereby increasing the Fowler angle 92).

If a caregiver has activated the full Fowler lockout control 100a (FIGS. 4 and 5), then the patient's pressing on either of the Fowler controls 86a or 86b does not result in any motion of the Fowler section 40. If the caregiver has activated the partial Fowler lockout control 100b, then the patient's pressing on the Fowler lower control 86b only results in controller 76 lowering the Fowler section 40 if, and so long as, the Fowler angle remains above or equal to the minimum Fowler angle 92 associated with partial Fowler lockout control 100b. Pressing the Fowler raise control 86a causes controller 76 to raise the Fowler section 40 upwardly, regardless of whether or not the partial Fowler lockout 100b has been activated or not. Pressing the gatch raise control 86c causes controller 76 to raise the gatch and pressing the gatch lower control 86d causes the controller 76 to lower the gatch, provided that neither of these controls have been locked out by a separate gatch lockout discussed in more detail below.

In addition to specifying the minimum Fowler angle 92 that a patient may reach when partial fowler lockout 100b is activated, motion messages 96 may also or alternatively include data that specifies other endpoints for any of the actuators 80a, 80b, 82, and/or 84, both in situations when a corresponding lockout has been activated and in situations when a corresponding lockout has not been activated. Thus, for example, when no lockouts are activated and a user uses Fowler controls 86a-b, controller 76 is configured to move the Fowler section 40 through a range of motion that is defined by a maximum angle and a minimum angle. Either or both of these angles may be adjusted via a motion limit message. Similarly, when a user presses on gatch raise control 86c and gatch lower control 86d, controller 76 is configured to raise and lower the gatch through a range of motion that is defined by maximum and minimum angles (or maximum and minimum heights). Either or both of these angles or heights may be adjusted by a motion limit message.

FIG. 7 illustrates a control panel 112 that may be incorporated into one or more of the user interfaces 42 that are intended to be used by caregivers (e.g. footboard user interface 42a and/or outer siderail user interface 42c), rather than by the patient. If incorporated into footboard user interface 42a, control panel 110 may replace all or a portion of the touchscreen controls shown in FIGS. 4 and 5, or it may provide a set of dedicated controls 48 for controlling patient support apparatus 20 that supplement the controls of touchscreen 46.

Control panel 112 includes a plurality of dedicated controls 48. Amongst these dedicated controls 48 is a Fowler raise control 86a, a Fowler lower control 86b, a gatch raise control 86c, a gatch lower control 86d, a litter deck raise control 86e, and a litter deck lower control 86f. Unless a corresponding lockout 100 is activated, pressing on any of the motion controls 86a-d causes the controller 76 to move the corresponding actuator(s) in the manner corresponding to the particular motion control 86 that has been activated (e.g. pressing Fowler raise control 86a causes controller 76 to activate the Fowler actuator 82 in a manner that raises the Fowler section 40 upwardly, thereby increasing the Fowler angle 92).

When a user presses on the litter deck raise control 86e, controller 76 activates the lift actuators 80a and 80b such that they raise litter frame 28. If the user keeps pressing on the litter deck raise control 86e, controller 76 continues to raise litter frame 28 until it reaches a maximum height. Similarly, when a user presses on litter deck lower control 86f, controller 76 activates the lift actuators 80a and 80b such that they lower litter frame 28, and if the user keeps pressing on the litter deck lower control 86f, controller 76 continues to lower litter frame 28 until it reaches a minimum height. These maximum and minimum heights may be changed by a motion limit message 96 sent to patient support apparatus 20 that specifies one or both of a new maximum height and a new minimum height.

FIG. 7 also illustrates a set of lockout controls 100, including a Fowler motion lockout control 100a, a partial Fowler motion lockout control 100b, a gatch motion lockout control 100c, and a litter deck motion lockout control 100d. These controls operate in the same manner discussed above with respect to FIGS. 4 and 5. The graphical representation 106 of FIG. 7 associated with partial Fowler motion lockout control 100b, however, does not change in response to new motion limit messages 96, but instead remains the same, regardless of the specific value used for the minimum Fowler angle 92. This differs from the graphical representation 106 of FIGS. 4 and 5 which changes in response to changing minimum (and/or maximum) Fowler angle limits. It will be understood by those skilled in the art that either static graphical representations 106 (e.g. FIG. 7) or dynamic graphical representations 106 (e.g. FIGS. 4 and 5), or a combination of both, may be used on patient support apparatuses 20.

It will be understood by those skilled in the art that controller 76 can be programmed to implement any new motion limits received from a motion limit message 96 in a variety of different manners. In at least one manner, the motion limit message 96 specifies the height, encoder counter, or voltage associated with the new motion limit and controller 76 monitors the sensor(s) 88 associated with the corresponding actuator to determine when the new motion limit is reached. Once reached, controller 76 stops further activation of the corresponding actuator in that direction.

It will further be understood by those skilled in the art that either patient support apparatuses 20 or any of the remote devices 54 (e.g. 54a, 54b, 54c, etc.) adapted to communicate with the patient support apparatuses 20 may be programmed with a translation function that translates a desired height limit and/or angle limit into a corresponding encoder value or voltage value. Thus, for example, if an authorized administrator has accessed the motion limit software application on server 54, the administrator may wish to change all of the patient support apparatuses within the healthcare facility to be able to lower their litter decks to within twelve inches of the floor. However, the administrator may not know what the encoder count is for the encoder sensors 88 of lift actuators 80a and 80b that corresponds to a height of twelve inches. The motion limit software application running on server 54 may therefore be equipped with a translation function that translates the twelve inch desired minimum height to an encoder value that is then sent to patient support apparatuses 20 in a motion limit message. In some embodiments, the translation function is implemented through the use of a table stored in memory that matches encoder values (or voltages from potentiometers) to heights. A table may be stored for each actuator 80a, 80b, 82, and 84, and the table may be changed to correlate angles to encoder counts, rather than heights to encoder counts, for some of the actuators (e.g. the Fowler actuator 82).

Still further, in some embodiments, servers 54a and/or 54b (or portable electronic device 54c) store separate tables for each model of patient support apparatuses 20 used within the healthcare facility. In such embodiments, different models of patient support apparatuses 20 may have different encoder values (or voltages) for a given height and/or for a given angle. In other words, a model X patient support apparatus 20 may have an encoder value of 1000 when the Fowler angle 92 is at thirty-five degrees, while a model Y patient support apparatus 20 may have an encoder value of 1200 when the Fowler angle 92 is at thirty-five degrees. If the user wants to set the minimum Fowler angle equal to thirty-five degrees for all patient support apparatuses 20 within the healthcare facility, the motion limit software application running on server 54a (or remote devices 54b or 54c) only asks the user to input a desired angle. It does not ask the user to input an encoder or voltage value. Once the desired angle is input, the software application converts that angle into the value of 1000 for the model X patient support apparatuses and a value of 1200 for the model Y patient support apparatuses. The software application then sends motion limit messages 96 to the model X patient support apparatuses 20 with a value of 1000 and motion limit messages 96 to the model Y patient support apparatuses 20 with a value of 1200.

As noted previously, in some embodiments, the translation function may be incorporated into each of the patient support apparatuses 20. In such embodiments, the motion limit message need only specify a height limit or an angular limit, and controller 76 includes a table, algorithm, or other data structure to convert the desired height or angular limit into an encoder value, voltage value, or other value corresponding to the desired height of angular limit. Once converted, controller 76 monitors the outputs from the corresponding sensor 88 and stops further motion of the actuator in its current direction when the encoder value, voltage value, or other value is reported by sensor 88.

As an alternative or supplemental manner of changing one or more of the motion limits of one or more of its actuators, controller 76 of patient support apparatus 20 is configured in some embodiments to receive a motion limit message via configuration transceiver 114. Configuration transceiver 114 is a transceiver that is powered by the electromagnetic energy received from a transmitting device. In other words, configuration transceiver 114 is adapted to operate when power to patient support apparatus 20 is absent. Configuration transceiver 114 can therefore receive a motion limit message and store it in second memory 117 when it is unpowered. An authorized technician, or other individual, who possesses a configuration tool that is adapted to communicate with and power transceiver 114 can therefore configure the motion limits of the patient support apparatus 20 even when the patient support apparatus 20 is unpowered.

This enables the patient support apparatus 20 to have it motion limits configured while it is in a warehouse, factory, or the like, prior to being installed at a healthcare facility.

In some embodiments, the configuration tool used by a technician to communicate a motion limit message 96 to configuration transceiver 114 is implemented in the same manner as the off-board configuration device 128 disclosed in commonly assigned U.S. patent application Ser. No. 62/543,094 filed Aug. 9, 2017, by inventors Marco Constant et al. and entitled FIELD CONFIGURABLE PATIENT SUPPORT APPARATUSES, the complete disclosure of which is incorporated herein by reference. Configuration transceiver 114 and second memory 117 may be implemented in the same or a similar manner as the communication circuitry 98 disclosed in the aforementioned '094 application. Still other manners of implementing memory 117 and transceiver 114 may be used.

Once the motion limit message 96 is communicated to transceiver 114 and second memory 117, it remains there until patient support apparatus 20 is powered on (memory 117 is a nonvolatile memory, such as, but not limited to, flash memory). After being powered on, controller 76 reads the motion limit message 96 stored in second memory 117, transfers the relevant contents to memory 78, and implements the motion limit(s) contained within the message 96 when activating actuators 80a, 80b, 82, and/or 84.

Although patient support apparatus system 52 has been described above as having motion limit messages 96 originate from one or more of the remote devices 54a-c in response to a user accessing the motion limit software application(s) executed thereon, it will be appreciated that in some embodiments, patient support apparatus system 52 may be modified to have one or more motion limit messages 96 automatically sent without user intervention. That is, rather than a user causing a motion limit message 96 to be sent to one or more patient support apparatuses 20, one or more of the remote devices 54a-c may be programmed to automatically send a motion limit message 96 in response to one or more user-defined conditions. For example, in some embodiments, local server 54a is programmed to automatically communicate with EMR server 62c and ADT server 62a to determine if a patient on a particular patient support apparatus 20 has one or more predefined medical conditions identified by administrators of the healthcare facility. If the patient does, the server 54a is programmed to automatically send a motion limit message 96 to that particular patient support apparatus 20 that limits the motion of that patient support apparatus 20 in a manner that the administrators of that healthcare facility have deemed helpful for patients having that particular predefined medical condition (or set of medical conditions). In this manner, patients having predefined medical conditions automatically have their patient support apparatus motion limits set to limits that are designed to treat or accommodate such patients.

The automatic correlation and implementation of motion limits with specific patients is implemented in the following manner in at least some embodiments. ADT server 62a stores patient assignments to rooms. Patient support apparatus server 54a receives room locations from patient support apparatuses 20 when the patient support apparatuses 20 communicate the unique identifiers from their adjacent locators 70. As noted, patient support apparatus server 54a includes a table, or access to a table, that correlates these identifiers to specific rooms and/or bays within rooms. By querying ADT server 62a for which patient is in which room, patient support apparatus server 54a learns which patient is associated with which room and/or bay, and thereby is able to correlate individual patients to individual patient support apparatuses 20. After learning a patient's identity from the ADT server 62a, the patient support apparatus server 54a sends an inquiry to the EMR server 62c to determine if the patient has any conditions that the healthcare facility has deemed a triggering condition for changing the motion limits on the patient support apparatus. If so, patient support apparatus server 54a sends the appropriate motion limit message 96 to the corresponding patient support apparatus 20.

Figure 8:
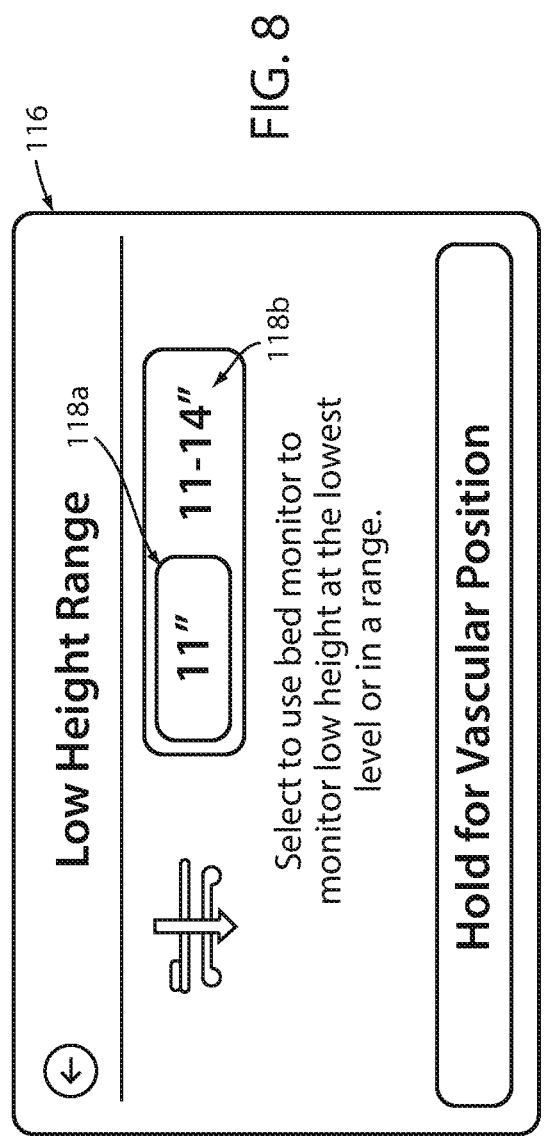
FIG. 8 is an illustrative screen shot of low height motion monitoring screen that is displayable on the display of the patient support apparatus of FIG. 1.

FIG. 8 illustrates a motion monitoring screen 116 that may be displayed on touchscreen 46 of patient support apparatus 20. Motion monitoring screen 116 allows a user to implement a motion monitoring function of patient support apparatus 20. Specifically, the screen 116 shown in FIG. 8 illustrates a litter height monitoring feature. If a user selects a first height control 118a, controller 76 monitors the current height of litter frame 28 and issues an alert if the height is changed from the height corresponding to first height control 118a (e.g. 11 inches in the illustrated embodiment). If a user selects a second height control 118b, controller 76 monitors the current height of litter frame 28 and issues an alert if the height is changed from the height, or in this case, the ranges of heights corresponding to second height control 118b (e.g. between 11 and 14 inches). Although FIG. 8 illustrates only two height controls 118 having two specific height values (or height range values), it will be understood that screen 116 may be modified to include additional and/or different height values and/or height range values.

The alerts issued by controller 76 may take on a variety of different forms and may be configured by a user utilizing one of user interfaces 42, such as footboard user interface 42a. The alerts include one or more lights, icons, or other indicators on patient support apparatus 20 whose illumination state is changed (e.g. turned on, changed to a different color, changed from steady to flashing, etc.) and/or one or more sounds emitted from patient support apparatus 20. The alerts may also include controller 76 sending a message to patient support apparatus server 54a via network transceiver 102, wherein patient support apparatus server 54a sends the alerts to one or more mobile electronic devices (e.g. device 54c) carried by one or more caregivers. The alerts may also include controller 76 issuing an alert that is communicated by headwall transceiver 85 to nurse call outlet 72 and from nurse call outlet 72 to nurse call system server 62b. Still other types of alerts may be issued.

Patient support apparatus 20 may include additional motion monitoring screens 116 similar to the one illustrated in FIG. 8, but targeted toward one or more of the other actuators of patient support apparatus 20 (e.g. Fowler actuator 82 and/or gatch actuator 84). Such additional motion monitoring screens 116 allow a user to configure patient support apparatus 20 to issue an alert if one or more of the other actuators 82 or 84 move outside of a designated range of movement.

Patient support apparatus 20 may be configured to allow the specific values, or ranges of values, corresponding to one or more of the controls 118 to be changed. In some embodiments, patient support apparatuses 20 are adapted to receive a monitoring message. The monitoring message may be sent from one of remote devices 54 in the same manner as the motion limit messages 96. The monitoring messages, however, are unlike the motion limit messages 96 in that they do not prohibit certain types of movement. Instead, they specify what values, or ranges of values, of actuators 80a, 80b, 82, and/or 84 are to cause controller 76 to issue an alert. Further, unlike the motion limits that typically can only be changed by motion limit messages 96 sent from off-board devices 54, the motion alerting parameters can be changed by a user directly on-board patient support apparatus 20 using one or more of the user interfaces 42.

In still another embodiment, patient support apparatus 20 may be configured to transmit a low height message to an external device 54 even when the litter frame 28 is not at its lowest height. In this embodiment, a user is able to configure patient support apparatus 20 to send such a low height message when the litter frame 28 is within a range of heights (one of which is the lowest possible height). In this embodiment, the remote device 54 receives a positive indication that the patient support apparatus 20 is in a low height state when, in fact, it may not necessarily be at its lowest height (although it is within the range specified by the user). If the litter frame 28 moves out of this range, patient support apparatus 20 stops sending the low height message and/or sends an out-of-low-height message. In still another embodiment, instead of sending a low height message to external device 54 when litter frame 28 is positioned within a range of heights, patient support apparatus 20 can be configured to send an out-of-low-height message only when the litter frame 28 is positioned outside a range of heights. In either embodiment, external device 54 is apprised of litter frame 28 moving out of its lowest height only when litter frame 28 has moved out of a range of low heights, rather than the single lowest height possible. Further, in either embodiment, controller 76 can be configured to—either in addition to, or in lieu of, sending an out-of-low height message or an in-low-height message to a remote device—provide a local indication on patent support apparatus 20 that indicates that the patient support apparatus is either at its lowest height (or within its low height range), or out of its lowest height (or out of its low height range). The local indication may include any one or more of the following: changing an illumination state of a light on patient support apparatus 20, displaying a message, icon, and/or other indicator on a display, emitting a sound, or still other manners. Commonly assigned U.S. patent application Ser. No. 16/229,108 filed on Dec. 21, 2018, and entitled PATIENT SUPPORT APPARATUS USER INTERFACES, and U.S. patent application Ser. No. 62/783,305 filed Dec. 21, 2018, and entitled USER MODULE FOR A PATIENT SUPPORT APPARATUS, disclose a plurality of different ways of providing local indications at the patient support apparatus which may be utilized in the present disclosure. The complete disclosure of both of these applications is incorporated by reference herein.

Still further, it will also be understood by those skilled in the art that any of the patient support apparatus 20 embodiments discussed herein can be modified to provide a local or remote indication that litter frame 28 is at its lowest height (or within a low height range) and to omit any modifiable motion limits (either for the litter frame 28 and/or the Fowler section 40). In other words, the present disclosure contemplates at least some embodiments of a patient support apparatus 20 that have only a single, unchangeable low height value, and that provide a local and/or remote indication when litter deck 28 is within its lowest height range (and/or provide a local and/or remote indication when litter deck 28 is outside of its lowest height range). The indication of litter frame 28 being within its low height range is, in some embodiments, easily viewable by a caregiver from a typical hospital hallway when the caregiver is looking into a typical hospital room containing the patient support apparatus 20, thereby enabling the caregiver to see if the patient support apparatus 20 is positioned at an acceptable height without necessarily having to enter the hospital room.

It should be apparent to those skilled in the art that the motion range monitoring features described herein are separate from the motion limiting features described above. That is, while some patient support apparatuses 20 may include both features, some other patient support apparatuses 20 according to the present disclosure may include the motion range monitoring features without being able to accommodate motion limit messages 96, while still other patient support apparatuses 20 may include the motion limiting feature, but not the range monitoring feature. In other words, the feature of changing the motion limits is separate and independent from the feature of issuing an alert when an actuator deviates from a value or range of values (or the feature of providing a notification when the actuator is currently at a desired value or within a desired range of values).

It will further be understood by those skilled in the art that still other motion limit messages beyond the ones identified herein may be communicated to patient support apparatus 20 from an external device. For example, in some embodiments, patient support apparatus 20 is configured to receive a motion limit message 96 that limits the angle at which an inflatable mattress 38 supported on support deck 30 turns a patient during lateral rotation therapy, or during other therapies and/or other movements of the patient. In such embodiments, the actuator is a blower, pump, or other source of pressurized air that inflates a bladder within mattress 38 in a manner that causes a portion or the patient's body (e.g. torso) to be rotated, turned, or otherwise repositioned. The blower, pump, or other source of pressurized air is contained within the mattress 38 itself, integrated into patient support apparatus 20 at a location external to mattress 38, temporarily supported on or by patient support apparatus 20, or located elsewhere. The motion limit message 96 specifies an angle the bladder creates, an air pressure for the bladder, and/or another value that limits how much rotation of the patient's body (or portion thereof) the mattress implements. Such motion limits messages 96 enable one or more limits on the movements of the patient carried out mattress 38 to be customized by authorized personnel for one or more patient support apparatuses 20.

Figure 11:
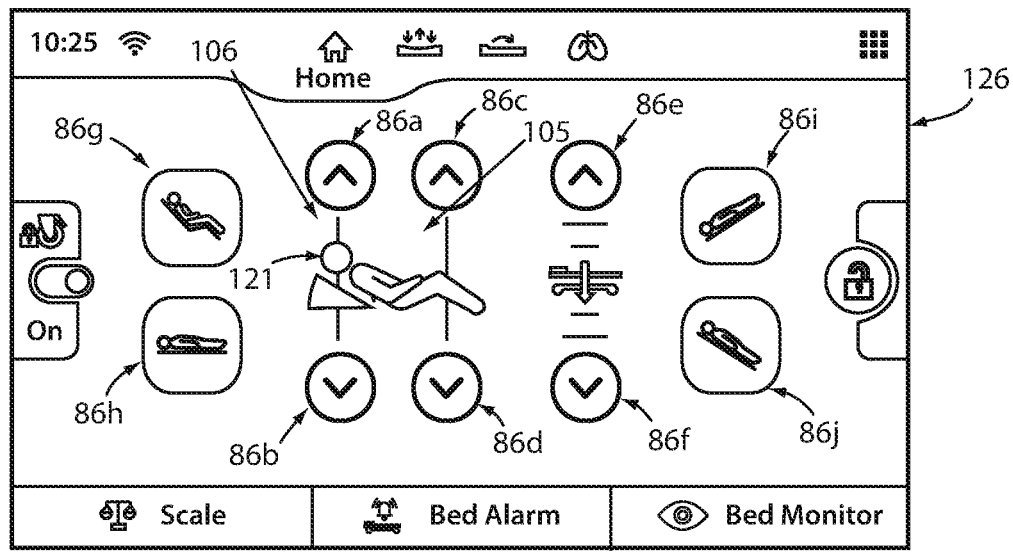
FIG. 11 is an illustrative screen shot of a main motion control screen displayable on the patient support apparatus of FIG. 1.

FIG. 11 illustrates one example of a motion control screen 126 that is displayable on display 46 of any of the patient support apparatus embodiments 20 disclosed herein. Motion control screen 126 is displayed by controller 76 in response to a user navigating to it. In some embodiments, motion control screen 126 may be the default screen which controller 76 initially displays on display 46 and/or it may be the screen to which controller 76 automatically returns after a predetermined time period of inactivity.

Motion control screen 126 includes motion controls 86 for controlling the movement of patient support apparatus 20. Specifically, it includes Fowler lift and lower controls 86*a* and 86*b*, gatch lift and lower controls 86*c* and 86*d*, litter frame lift and lower controls 86*e* and 86*f* (grayed out), a chair position control 86*g*, a flat position control 86*h*, a Trendelenburg control 86*i*, and a reverse Trendelenburg control 86*j*. In some embodiments of patient support apparatus 20, motion control screen 126 is displayed at footboard user interface 42*a* and the motion controls at user interfaces 42*b* and/or 42*c* are static controls (e.g. not part of a touchscreen). In other embodiments, motion control screen 126 may be displayed at any one or more of the user interfaces 42*a*, 42*b*, and/or 42*c*.

In at least some embodiments, controller 76 is adapted to change one or more aspects of motion control screen 126 in response to a user activating one or more of the lockouts 100a, 100b, 100c, and/or 100d. Further, in at least some embodiments, controller 76 is adapted to change one or more aspects of motion control screen 126 in response to different motion control limits being received. For example, in one embodiment, controller 76 displays a wedge 121 in a first color if the current Fowler angle is equal to or above the minimum angular threshold and the partial Fowler lockout 100b has not been activated; displays wedge 121 in a second color if the current Fowler angle is equal to or above the minimum angular threshold and the partial Fowler lockout 100b has been activated; displays wedge 121 in a third color (such as being grayed out or completely absent) if the current Fowler angle is below the minimum angular threshold and the partial Fowler lockout 100b has not been activated; and stops displaying wedge 121 completely (or grays it out) if full Fowler lockout 100a is activated. Further, the size and/or shape of wedge 121 is changed by controller 76 in response to the receipt of a new motion limit message that changes the minimum angular threshold of partial Fowler lockout control 100b (i.e. the angle subtended by wedge 121 can be changed to match that of the minimum Fowler lockout angle received in the new motion limit message). The changing of the size and/or shape of wedge 121 may also, or alternatively, be accompanied by changes in any one or more components of the patient icon 105 shown in FIG. 11 (e.g. shifting the head and torso section more upright when the minimum Fowler lockout angle is increased, and vice versa).

Additional changes in color may also be implemented on screen 126 in response to the activation of one or more lockout controls 100a-d, such as, but not limited to, changing the color of any controls 86a-h in response to the activation of one or more of the corresponding lockout controls 100a-d. Additionally, or alternatively, one or more portions of graphical representation 106 may have their color, size, and/or shape changed in response to the activation of one or more of lockout controls 100a-d.

It will also be understood that any of the screens 104, 104a, 104b, etc. displayed on display 46 can be modified in a variety of different manners. In some such modified embodiments, any of these screens may be modified to operate in accordance with, and/or display the content of, the control screens disclosed in commonly assigned U.S. patent application Ser. No. 16/229,108 filed on Dec. 21, 2018, and entitled PATIENT SUPPORT APPARATUS USER INTERFACES, the complete disclosure of which is incorporated herein by reference. Still other modifications are possible.

It will further be understood that any of the screens disclosed herein (e.g. settings screen 124, lockout screens 104a, b, c, d, motion control screen 126, motion monitoring screen 116) may consume the entire area of display 76 in some embodiments, while in other embodiments such screens may consume only a portion of the area of display 76. In those embodiments where the screen only consumes a portion of the area of display 76, those areas of display 76 that are not consumed by the screen may be filled with portions of another screen (e.g. one screen may be partially laid over another existing screen).

Still further, it will be understood that combinations of any of the elements of any of the above-described embodiments with any of the elements of any of the other described embodiments may be made.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A patient support apparatus comprising:
   a base;
   a litter frame supported on the base;
   a support deck supported on the litter frame and configured to support a patient thereon;
   an actuator adapted to raise and lower the litter frame with respect to the base;
   a movement control adapted to cause the actuator to move the litter frame when the movement control is activated by a user;
   a memory having a first setting and a second setting stored therein, the first setting corresponding to a first range of motion for the litter frame and the second setting corresponding to a second range of motion for the litter frame; and
   a controller in communication with the memory, the actuator, and the movement control, the controller adapted to select the first setting or the second setting, the controller further adapted to prevent movement of the litter frame outside the first range of motion if the controller selects the first setting and to prevent movement of the litter frame outside the second range of motion if the controller selects the second setting.

2. The patient support apparatus of claim 1 further comprising a transceiver adapted to communicate with an external device and to receive a motion limit message from the external device, the controller selecting the first setting or the second setting based on the motion limit message.

3. The patient support apparatus of claim 2 wherein the external device is a server on a healthcare facility computer network.

4. The patient support apparatus of claim 2 wherein the motion limit message includes at least one of the first setting and the second setting and the controller is adapted to store the at least one of the first setting and the second setting in the memory.

5. The patient support apparatus of claim 2 wherein the first range of motion defines a first minimum height and the second range of motion defines a second minimum height, and the controller is adapted to prevent lowering of the litter frame below the first minimum height when the controller selects the first setting and to prevent lowering of the litter frame below the second minimum height when the controller selects the second setting.

6. The patient support apparatus of claim 1 further comprising a transceiver adapted to communicate with an external device, and wherein the controller is configured to select the first setting in the absence of receiving a motion limit message from the external device instructing the controller to select the second setting.

7. The patient support apparatus of claim 1 further comprising:

a backrest actuator adapted to pivot a backrest of the support deck;

a lockout control adapted to be activated by the user; and wherein the memory includes a third setting corresponding to a third range of motion for the backrest and a fourth setting corresponding to a fourth range of motion for the backrest, and wherein the controller is further adapted to select the third or the fourth setting when the lockout control is activated, the controller preventing pivoting of the backrest outside the third range of motion if the controller selects the third setting and the controller preventing pivoting of the backrest outside the fourth range of motion if the controller selects the fourth setting.

8. The patient support apparatus of claim 7 wherein the controller is further configured to prevent pivoting of the backrest outside a fifth range of motion if the lockout control is not activated, the fifth range of motion being larger than both the third and fourth ranges of motion.

* * * * *